(12) United States Patent
Deleuze-Masquefa et al.

(10) Patent No.: US 10,689,384 B2
(45) Date of Patent: Jun. 23, 2020

(54) IMIDAZO[1,2-A]QUINOXALINES AND DERIVATIVES THEREOF FOR THE TREATMENT OF CANCER

(71) Applicants: Universite de Montpellier, Montpellier (FR); Centre National de la Recherche Scientifique (CNRS), Paris (FR); Axlr, Satt du Languedoc Roussillon, Montpellier (FR)

(72) Inventors: Carine Deleuze-Masquefa, Saint Jean De Vedas (FR); Pierre-Antoine Bonnet, Montpellier (FR); Pierre Cuq, Maurin (FR); Cindy Patinote, Montpellier (FR)

(73) Assignees: Universite de Montpellier, Montpellier (FR); Centre National de la Recherche Scientifique (CNRS), Paris (FR); Axlr, Satt du Languedoc Roussillon, Montpellier (FR)

( * ) Notice: Subject to any disclaimer, the term of this patent is extended or adjusted under 35 U.S.C. 154(b) by 0 days.

(21) Appl. No.: 15/541,056

(22) PCT Filed: Dec. 30, 2015

(86) PCT No.: PCT/EP2015/081397
§ 371 (c)(1),
(2) Date: Jun. 30, 2017

(87) PCT Pub. No.: WO2016/107895
PCT Pub. Date: Jul. 7, 2016

(65) Prior Publication Data
US 2018/0016278 A1 Jan. 18, 2018

(30) Foreign Application Priority Data
Dec. 31, 2014 (FR) .................................... 14 63480

(51) Int. Cl.
*C07D 487/04* (2006.01)

(52) U.S. Cl.
CPC ................... *C07D 487/04* (2013.01)

(58) Field of Classification Search
CPC .................................................. C07D 487/04
USPC ....................................................... 514/250
See application file for complete search history.

(56) References Cited

U.S. PATENT DOCUMENTS

| 4,689,338 | A | 8/1987 | Gerster | |
|---|---|---|---|---|
| 8,378,098 | B2 * | 2/2013 | Deleuze-Masquefa | C07D 487/04 544/346 |
| 8,513,250 | B2 * | 8/2013 | Escaich | C07D 487/04 514/250 |
| 2003/0022898 | A1 | 1/2003 | Burke et al. | |
| 2006/0025419 | A1 | 2/2006 | Richmond et al. | |

FOREIGN PATENT DOCUMENTS

| FR | 2921927 A1 | 4/2009 | | |
|---|---|---|---|---|
| WO | 93/04066 A1 | 3/1993 | | |
| WO | 2006/070408 A2 | 12/2006 | | |
| WO | 2007/109813 A1 | 9/2007 | | |
| WO | 2007/087250 A2 | 1/2008 | | |
| WO | WO-2008117225 A2 * | 10/2008 | .......... | C07D 471/04 |
| WO | 2009/043934 A1 | 4/2009 | | |
| WO | WO-2009043934 A1 * | 4/2009 | .......... | C07D 487/04 |
| WO | 2010/124826 A1 | 11/2010 | | |
| WO | WO-2010124826 A1 * | 11/2010 | .......... | C07D 487/02 |

OTHER PUBLICATIONS

Bonnard, V. et al. Synthesis and Evaluation of in Vitro Antitumoral Activity of Imidazo[1,2-?]Quinoxaline and Imidazo [1,5-?]Quinoxaline Derivatives, (RICT 2005, Paris).
Catarzi, D. et al., Structure-Activity Relationships of 1,2,4-Triazolo[1,5-?]quinoxalines and Their 1-Deaza Analogues Imidazo[1,2-?]quinoxalines at the Benzodiazepine Receptor, J. Med. Chem., 1994, vol. 37, pp. 2846-2850.
Colotta, V. et al., Synthesis of some tricyclic heteroaromatic systems and their A1 and A2a adenosine biding activity, Eur. J. Med. Chem, 1995, vol. 30, pp. 133-139.
Deleuze-Masquéfa, C. et al., Design and synthesis of novel imidazo[1,2-?]quinoxalines as PDE4 inhibitors, Bioorganic & Medicinal Chemistry, 2004, vol. 12, pp. 1129-1139.
Deleuze-Masquéfa, C. et al., New imidazo[1,2-?]quinoxalines derivatives: Synthesis and in vitro activity against human melanoma, European Journal of Medicinal Chemistry, 2009, vol. 44, pp. 3406-3411.
Gattacceca, F. et al., Imiqualines: promising anticancer molecules biding colchicine site on tubulin, Faseb J., 2013, vol. 27, Ib584.
Khier, S. et al., Metabolism and Pharmacokinetics of EAPB0203 and EAPB0503, Two Imidazoquinoxaline Compounds Previously Shown to Have Antitumoral Activity on Melanoma and T-Lynphomas, Drug Metab Dispos 2010, vol. 38, No. 10, pp. 1836-1847.

(Continued)

*Primary Examiner* — Rita J Desai
(74) *Attorney, Agent, or Firm* — Banner & Witcoff, Ltd.

(57) ABSTRACT

The invention relates to imidazo[1,2-a]quinoxaline compounds of formula (I) for the treatment of cancer, the pharmaceutical compositions comprising said chemical compounds, and the therapeutic uses thereof.

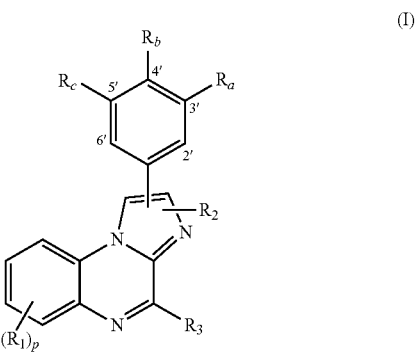

14 Claims, 1 Drawing Sheet

(56) References Cited

OTHER PUBLICATIONS

Khier, S. et al., Pharmacology of EAPB0203, a novel imidazo[1,2-?]quinoxaline derivative with anti-tumoral activity on melanoma, Eur. J. Pharm. Sci. 2010, vol. 39, pp. 23-29.

Khier, S. et al., Quantitation of imidazo[1,2-?] derivatives in human and rat plasma using LC/ESI-MS, J. Separation Sci. 2009, vol. 32, pp. 1363-1373.

Lafaille F. et al., Structural characterization of in vitro metabolites of the new anticancer agent EAPB0503 by liquid chromatography-tandem mass spectrometry, J. Pharm. Biomed. Anal. 2014, vol. 88, pp. 429-440.

Lafaille, F. et al., Characterization of a New Anticancer Agent, EAPB0203, and Its Main Metabolites: Nuclear Magnetic Resonance and Liquid Chromatography-Mass Spectrometry Studies, Anal Chem., 2012, vol. 84, pp. 9865-9872.

Moarbess, G. et al., In vitro and in vivo anti-tumoral activities of imidazo[1,2-?]quinoxaline, imidazo[1,5-?]quinoxaline, and pyrazolo[1,5-?]quinoxaline derivatives, Bioorg. Med. Chem., 2008, vol. 16, pp. 6601-6610.

Morjaria, S. et al., Impairment of TNF-? Production and Action by Imidazo[1,2-?] Quinoxalines, A Derivative Family Which Displays Potential Anti-Inflammatory Properties, International Journal of Immunopathology and Pharmacology, 2006, vol. 19, No. 3, pp. 525-538.

Saliba, J. et al., EAPB0503, a novel imidazoquinoxaline derivative, inhibits growth and induces apoptosis in chronic myeloid leukemia cells, Anti-Cancer Drugs, 2014, vol. 25, No. 6, pp. 624-632.

Zurbonsen, K. et al., Antiproliferative Effects of Imidazo[1,2-?]pyrazine Derivatives on the Dami Cell Line, Biochemical Pharmacology, 1997, vol. 54, pp. 365-371.

Zurbonsen, K. et al., Apoptotic effects of imidazo[1,2-?]pyrazine derivatives in the human Dami Cell Line, European Journal of Pharmacology, 1997, vol. 320, pp. 215-221.

\* cited by examiner

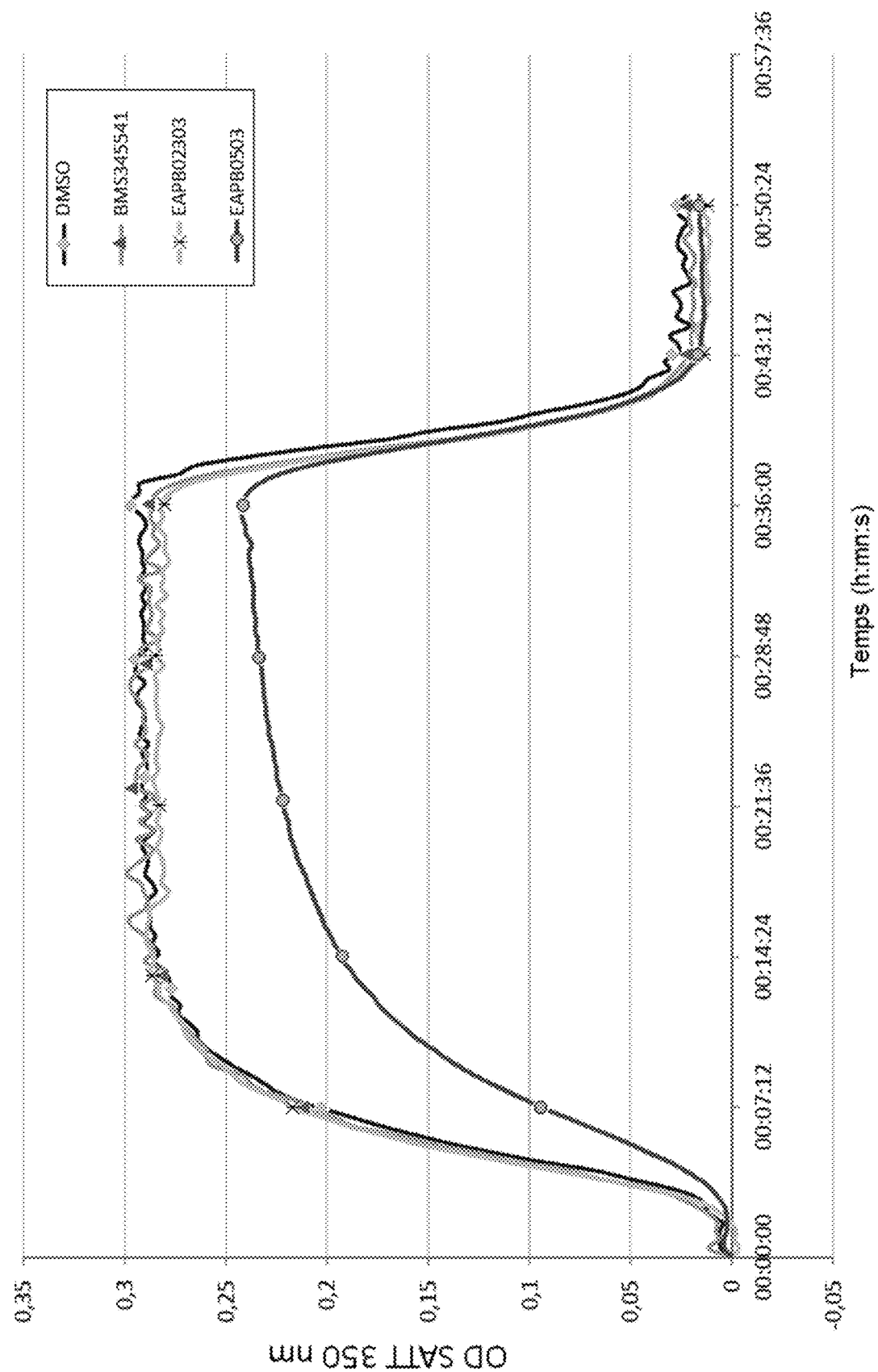

US 10,689,384 B2

IMIDAZO[1,2-A]QUINOXALINES AND DERIVATIVES THEREOF FOR THE TREATMENT OF CANCER

RELATED APPLICATION DATA

This application is a National Stage Application under 35 U.S.C. 371 of co-pending PCT application number PCT/EP2015/081397 designating the United States and filed Dec. 30, 2015; which claims the benefit of FR application number 1463480 and filed Dec. 31, 2014 each of which are hereby incorporated by reference in their entireties.

The present invention concerns imidazo[1,2-a]quinoxaline compounds for the treatment of cancers, pharmaceutical compositions comprising said compounds, and therapeutic uses thereof. The invention also concerns the use of imidazo[1,2-a]quinoxaline derivative compounds for the preparation of medicinal products for treating cancers and in particular for the treatment of melanomas and T-cell lymphomas.

| Contents of the invention | |
|---|---|
| INTRODUCTION | 3 |
| SUMMARY OF THE INVENTION | 7 |
| Definitions | 9 |
| DETAILED DESCRIPTION | 11 |
| Figures | 20 |
| Examples | 21 |
| General synthesis of imidazo[1,2-α]quinoxaline compounds | 21 |
| Experimental section | 23 |
| Chemistry | 23 |
| Procedure for addition at the 4-position | 23 |
| Procedure for addition of ammonia | 23 |
| Procedure for addition of methylamine | 24 |
| General bromination procedure | 28 |
| General procedure for the Suzuki cross-coupling reaction | 30 |
| General procedure for the deprotection reaction | 34 |
| (2S)-2-((1-(3,4-Dimethoxyphenyl)imidazo[1,2-α]quinoxalin-4-yl)amino)propanoic acid (EAPB 02219) | 38 |
| (2S)-2-((1-(3,4-Dimethoxyphenyl)imidazo[1,2-α]quinoxalin-4-yl)amino)-3-methylbutanoic acid (EAPB 02221) | 38 |
| (2S)-2-Amino-5-((1-(3,4-dihydroxyphenyl)imidazo[1,2-α]quinoxalin-4-yl)amino)pentanoic acid (EAPB 02325) | 38 |
| Biology: Study of the activity of the compounds on 15 tumor lines, In vitro cytotoxicity study | 38 |
| Protocol | 38 |
| Materials and methods | 47 |
| Study of the effect of the compounds on the polymerization of purified tubulin | 47 |
| CLAIMS | 48 |

INTRODUCTION

Given the low efficacy of a great majority of conventional anticancer agents in the treatment of cancers such as prostate cancer, colon cancer, breast cancer, melanoma and lymphoma, research is directed toward new therapeutic strategies. Indeed, to succeed in overcoming the problems of resistances and of metastases, encountered more and more often in this type of disease, represents an important challenge for research.

Great hopes have been placed in immunotherapy, which contrary to other therapies makes it possible to treat the body as a whole and can eliminate the tumor cells disseminated throughout the body. Among the various immunotherapeutic approaches, the discovery of imiquimod (Aldara®), the first immunomodulating anticancer agent, effective notably against certain skin cancers such as melanoma, made it possible to take a step forward on this new pathway. Imiquimod is a nitrogen-containing tricyclic molecule of the imidazoquinoline family (WO 2006/070408, U.S. Pat. No. 4,689,338). It is known primarily for its antiviral activity against certain viruses such as herpes simplex II, Sendai virus and papilloma virus. The latest publications on this molecule also demonstrate substantial immunomodulatory antitumor activity on skin cancers such as basal cell carcinoma, actinic keratosis and melanoma. More recent studies also showed efficacy against cutaneous metastases and vascular tumors. Imiquimod is thus the first of a new class of anticancer drugs called innate and acquired immune response modifiers, the mechanism of action of which differs from all known anticancer agents, e.g. nitrogen mustard, nitrosourea, alkylating agents, organoplatinum, etc.

However, a certain number of documents of the prior art disclose other quinoxaline derivatives for various therapeutic applications.

Hence, Deleuze-Masquéfa et al. (Bioorganic & Medicinal Chemistry 12, 1129-1139, 2004) describe imidazo[1,2-a]quinoxaline derivatives as phosphodiesterase-4 (PDE4) inhibitors. Unlike imiquimod, these molecules inhibit the production and the effects of TNF-α in vitro and thus they seem to have a mode of action different from imiquimod. These derivatives may be of interest for their anti-inflammatory properties (Mojaria et al. International Journal of Immunopathology and Pharmacology, 19, 2, 77-90, 2006). Anticancer activity, and a fortiori activity on melanomas or lymphomas, is neither described nor suggested in these documents. Indeed, it is described that the cytoprotective properties of the compounds cannot be correlated with their (IPDE4 activity. The compounds would act by activating the p38MAPK pathway and inhibiting the PI3K pathway. They would thus inhibit TNF-α action and production, making these drugs potential anti-inflammatory compounds. The effect of the compounds concerns protection from cell death induced by TNF-α on immune cells, which does not make it possible to envisage a priori the effects of the compounds concerning their direct cytotoxic activity on cancer cells.

Bonnard et al. (RICT 2005, Paris) describe the synthesis and the evaluation for their antitumor activity of imidazo[1,2-a]quinoxaline derivatives. The structure of the compounds tested is however not described.

US 2003/0022898 describes derivatives also having anti-inflammatory activity, including a 4-(2'-aminoethyl)-amino-1,8-dimethylimidazo(1,2-a)quinoxaline compound. This compound is also described as having antimelanoma activity in the document US 2006/0025419.

Colotta et al. (Eur. J. Med. Chem, 30, 133-139, 1995) describe various compounds, including imidazo[1,2-a]quinoxalines. Triazoloquinoxalines are described as binding to the adenosine receptor. Particular applications of imidazo [1,2-a]quinoxalines are not described.

Catarzi et al. (J. Med. Chem., 37, 2846-2850, 1994) describe triazoloquinoxalines and imidazoquinoxalines binding to the benzodiazepine receptor. The molecules binding to the benzodiazepine receptor are generally recognized for their anxiolytic activities. This document does not describe applications to cancer.

WO 93/04066 describes imidazoquinoxalinol compounds binding specifically to GABAa receptors. Only therapeutic uses as sedatives, anxiolytics, anticonvulsants, etc., are envisaged. Applications in other therapeutic fields, in particular for the treatment of cancers, are neither described nor suggested by this document.

Zurbonsen et al. (European Journal of Pharmacology, 320, 215-221, 1997 and Biochemical Pharmacology, 54, 365-371, 1997) describe imidazo[1,2-a]pyrazine derivatives that have inhibitory activity on phosphodiesterases and are capable of inducing apoptosis in a leukemia cell line. It should be noted, however, that not all phosphodiesterase inhibitors have anticancer activity. Moreover, the compounds of the present invention are distinguished by high activity demonstrated in in vitro and in vivo tests on both lymphoma and melanoma.

WO 2007/109813 relates to imidazoquinoxalines having immunomodulatory activity. Only applications in the field of adjuvants and vaccines are described. This document envisages potential applications in many therapeutic fields, including cancer, but no in vitro or in vivo data confirms any anticancer activity.

WO 2007/087250 describes 5-lipoxygenase (LO) inhibitors. Applications in the field of cancer are not described.

The first imidazo[1,2-a]quinoxalines forming the subject-matter of FR 2,921,927 (equivalent to WO 2009/043934 filed one year later) have an advantageous activity, novel and unexpected in 2007, on various cancers such as melanoma and T-cell lymphoma. The activities measured on various cell lines representative of these cancers show activities ($IC_{50}$) of the micromolar order. Thus, direct cytotoxic activity with $IC_{50}$ values of the micromolar order was demonstrated in vitro on various human tumor cell lines for the compounds disclosed in this patent application: melanoma, breast, colon, B lymphoma and adult T-cell leukemias/lymphomas (ATL) (Table 1) (Moarbess et al.), Bioorg. Med. Chem. 16, 6601-6610, 2008).

Several results concerning the in vivo anticancer activity of molecules derived directly from FR 2,921,927 have been published (Moarbess et al., Bioorg. Med. Chem. 16, 6601-6610, 2008; Khier et al., J. Separation Sci. 2009, 32, 1363-1373; Khier et al., Drug Metab Dispos 2010, 38(10), 1836-1847; Khier et al., Eur. J. Pharm. Sci. 2010, 39(1-3): 23-29; Lafaille et al., Anal Chem. 2012, 84(22):9865-72; Lafaille F. et al., J. Pharm. Biomed. Anal. 2014, 88, 429-440).

Furthermore, a major problem posed by the development of anticancer agents relates to their toxicity, linked to their lack of specificity. Indeed, many anticancer agents act by disrupting general physiological cellular mechanisms such as inhibition of tubulin, for example. Tubulin is indeed present in all cells and is essential to the cell multiplication process, whether physiological or pathological, in the case for example of cancers. Alteration of the physiological processes involved in cell multiplication can generate notable side effects and should be avoided. Indeed, the first imidazo[1,2-a]quinoxalines synthesized have this deleterious effect of tubulin inhibition.

Thus, studies of inhibition of tubulin polymerization on purified tubulin fractions showed powerful inhibition by certain compounds disclosed in FR 2,921,927 (Gattacceca et al., Faseb J., 2013, 27, Ib584; Saliba et al., AntiCancer Drugs, 2014, 25, 624-632.).

However, the compounds of the present invention have an efficacy of a completely different level than the first imidazo [1,2-a]quinoxaline derivatives specifically described in FR 2,921,927, with $IC_{50}$ values on the order of 10 or so nanomoles, indeed nanomolar for some. Moreover, these new molecules no longer have a significant effect on tubulin. The molecules according to the present invention, in fact, make it possible to leave tubulin polymerization unaltered and thus to avoid the side effects associated therewith. Indeed, since microtubule activity may also be blocked in the case of compounds that inhibit tubulin polymerization, any other cellular activity requiring it, such as intraneuronal axonal transport, phagocytosis or leukocyte chemotaxis, for example, will also be inhibited. Moreover, the compounds of the present invention have shown significant activity on tumors tested in vitro. These effects are thus quite surprising and make it possible to envisage new therapies, particularly anticancer therapies.

The novel properties appear linked to a family of molecules having precise characteristics in terms of groups on the aromatic phenyl ring attached at the 1- or 2-position of the imidazol of the imidazo[1,2-a]quinoxaline heterocycle.

Thus, to remedy the disadvantages of the state of the art, the present invention proposes novel imidazo[1,2-a]quinoxaline derivative compounds for the treatment of cancers without specific distinction of the location of the tumor or tumors. These compounds may be used for the preparation of medicinal products for treating cancers.

SUMMARY OF THE INVENTION

The present invention relates to a compound of the general formula (I):

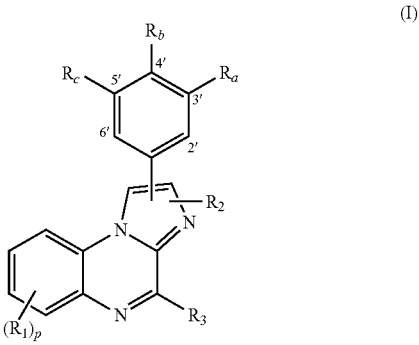

wherein:
the various $R_1$ independently represent a hydrogen or halogen atom or a group selected from hydroxy, $C_1$-$C_4$ alkyl, $C_1$-$C_4$ alkoxy, amino, $C_1$-$C_4$ alkylamino, $C_1$-$C_4$ dialkylamino, cyano, —$CF_3$, —$OCF_3$, —$(CH_2)_nNR_4R_5$, —$NH$—$(CH_2)_nNR_4R_5$, —$(CH_2)_n$ $COR_4$, —$(CH_2)_nCO$—$NR_4R_5$, —$(CH_2)_nSO_2$—$NR_4R_5$, and —$(CH_2)_nCO_2R_4$ groups;

$R_2$ represents a hydrogen atom or a group selected from hydroxy and $C_1$-$C_2$ alkyl groups, preferably a hydrogen atom;

$R_3$ represents a halogen or a group selected from amino, $C_1$-$C_3$ alkylamino, $C_1$-$C_3$ dialkylamino, amine-($C_1$-$C_6$ alkyl)-amino, N-(tert-butyloxycarbonyl)amino-($C_1$-$C_6$ alkyl)-amino, piperidyl, N-(tert-butyloxycarbonyl)piperidyl groups, an amino group of an α-amino acid or an amino group of an α-amino acid side chain, $R_a$, $R_b$ and $R_c$ independently represent a hydrogen atom or a group selected from hydroxy, $C_1$-$C_4$ alkoxy, amino, $C_1$-$C_4$ alkylamino and $C_1$-$C_4$ dialkylamino groups;

n being 0, 1, 2, 3 or 4, preferably n being 0;

p being 1, 2, 3 or 4;

$R_4$ and $R_5$ independently represent a hydrogen atom or a $C_1$-$C_4$ alkyl group, preferably linear or branched;

provided that at least 2 of the residues $R_a$, $R_b$ and $R_c$ are different from H, or a pharmaceutically acceptable salt thereof.

$R_3$ is preferably a halogen or a group selected from amino, particularly methylamino, dimethylamino, ethylamino, diethylamino, aminomethylamino, aminoethylamino, aminopropylamino and aminohexylamino groups, and in particular a methylamino group.

The amino acid may be any natural amino acid, any nonnatural amino acid or any amino acid the side chain of which is modified. Advantageously, the amino acid may be selected from the group consisting of Gly, Ala, Val, Leu, Phe, Tyr, Ser, Lys, Orn, Arg, Glu, His, Trp, Pro, Thr, Cys, Met, Asn and Gln.

The present invention further relates to a method for manufacturing a compound of the invention characterized in that said method comprises:

a step of coupling the compound of the formula (V):

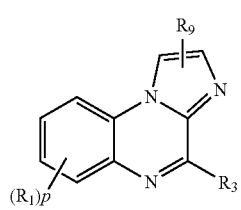

(V)

wherein $R_1$, $R_3$ and p are as defined above; and $R_9$ is a halogen atom;

with a suitable arylboronic acid (e.g. of type [Ph($R_a$,$R_b$, $R_c$)—B(OH)$_2$]), variously meta- and/or para-substituted by $R_a$, $R_b$ and/or $R_c$ groups as defined herein, under Suzuki conditions; and recovering, extracting and/or purifying the compound obtained according to the present invention.

The present invention also relates to a pharmaceutical composition comprising at least one compound according to the present invention and optionally a pharmaceutically acceptable carrier.

The present invention thus relates to a compound according to the present invention as a medicinal product.

Finally, the present invention relates to a compound according to the present invention for use in the treatment of at least one cancer.

Definitions

By "halogen" is meant in particular according to the present invention the following halogens: F, Cl, Br and I.

By "alkyl" is meant in particular according to the present invention linear or branched alkyl radicals, in particular $C_1$, $C_2$, $C_3$, $C_4$, $C_5$ or $C_6$ alkyl radicals, when the length of the chain is not specified, in particular methyl, ethyl, n-propyl, i-propyl, n-butyl, i-butyl or t-butyl radicals. This definition also applies to the alkyl moieties of cycloalkyl, alkoxy, acyl, aralkyl, alkylamino or thioalkyl radicals. Thus, by "$C_1$-$C_4$ dialkylamino" is meant that two $C_1$-$C_4$ alkyl groups are bound to the same amine. When the stereochemistry of an alkyl group is not specified (e.g. aminopropylamine), preferably it is a linear alkyl ("n-alkyl", i.e., amino-(n-propyl) amine) in the preceding specific case).

By "alkenyl" is preferably meant according to the invention a monovalent, unsaturated hydrocarbon chain containing at least one double bond, linear or branched, having 2 to 6 carbon atoms when the length of the chain is not specified, the representative elements of which are, for example, vinyl, 1-propenyl, 2-propenyl, isoprenyl, butenyl, pentenyl, hexenyl groups.

By "cycloalkyl" is advantageously meant according to the invention $C_3$-$C_7$ cycloalkyls when the number of carbons contained in the ring is not specified, more particularly cyclopropyl, cyclobutyl, cyclopentyl, cyclohexyl and cycloheptyl radicals.

By "aryl" is preferably meant according to the invention one or more aromatic rings having 6 to 10 carbon atoms when the number of carbons contained in the ring is not specified, which may be coupled or fused, in particular phenyl. This definition also applies to the aryl moiety of aralkyl radicals. The aralkyl group is preferably $(CH_2)_m$-phenyl, wherein m is between 0 and 4.

By "amino" or "amine" is meant a primary, secondary or tertiary amine, preferably —$NH_2$ or —$NH_3^+$ if it is a salt.

By "methylamino" or "alkylamino" is meant —$NH$—$CH_3$ or —$NH$-alkyl radicals.

By "aminoalkylamino" is meant —$NH$-alkyl-$NH_2$ radicals.

By "heterocycle" is advantageously meant according to the invention a $C_3$-$C_7$ ring, when the number of carbons contained in the ring is not specified, containing at least one heteroatom selected from nitrogen, oxygen or sulfur, in particular the heterocycles are selected from thienyl, furyl, quinolinyl, indolyl, pyrazole, pyrrole, pyridine, pyrimidine, imidazole.

By "cancer" is meant all malignant neoplastic formations, whatever the histological nature. Malignant tumors are divided into two main categories: carcinomas, of epithelial origin, and sarcomas, of conjunctive origin. Malignant tumors are made of atypical cells, invasive or disseminating, generally characterized by the ability to grow autonomously, an imprecise definition, an ability to invade nearby tissues and vessels and a tendency to disseminate by producing metastases. Notable cancers include cancers of the breast, prostate, pancreas, lungs, esophagus, skin, bladder, stomach, liver, uterus, colon and rectum.

By "solid cancer" is meant cancers having carcinoma or sarcomatype tumors. These cancers develop in any tissue.

By "liquid cancer" is meant leukemia or lymphomatype cancers. Leukemias are cancers of the blood and bone marrow, whereas lymphomas are cancers of the lymphatic system. These blood cancers thus result from a tumoral proliferation of blood cells. There thus exist acute and chronic leukemias of lymphatic system cancers (lymphomas, Hodgkin's disease and multiple myeloma). For example, leukemia appears when immature (precursor) blood cells (such as lymphocytes or leukocytes) become cancerous and unable to mature further or to specialize normally.

By "metastatic cancer" or "disseminated cancer" is meant tumors that produce migrating cancer cells through the body, via blood or lymphatic vessels, and that have colonized at least one other tissue (and thus are able to generate at least one new tumor).

By "secondary cancer" is meant cancers resulting from an anticancer treatment that is believed to be therapeutic.

By "melanoma" is meant a malignant tumor that develops at the expense of pigmented tissues, more especially those of the skin or eye.

By "lymphoma" is meant any tumor, generally malignant, due to proliferation of lymphoid tissue cells, developing especially in the spleen or ganglia.

By "pharmaceutically acceptable salt" is preferably meant according to the invention a salt of a pharmaceutically acceptable acid, i.e., with any nontoxic acid, including organic and inorganic acids. Such acids include acetic, benzenesulfonic, benzoic, citric, ethanesulfonic, fumaric, gluconic, glutamic, hydrobromic, hydrochloric, lactic, maleic, malic, mandelic, methanesulfonic, mucic, nitric, pamoic, pantothenic, phosphoric, succinic, sulfuric, tartaric and paratoluenesulfonic acids.

DETAILED DESCRIPTION

The $R_1$ group or groups represent, preferably and independently, a hydrogen atom, a halogen or a group selected from the groups methyl, ethyl, propyl, isopropyl, butyl, isobutyl, tert butyl, and —$(CH_2)_{n'}$—CH=CH—$(CH_2)_{n''}$ with n' and n" independently being between 0 and 4, $COOR_4$, $NR_4R_5$ and $OR_4$, $R_4$ and $R_5$ are defined above.

Preferably, p=0, 1, 2 or 3. Preferably, p=0.

Preferably, $R_2$ is a hydrogen atom.

Preferably, $R_a$ represents a hydrogen atom or a group selected from hydroxy and $C_1$-$C_4$ alkoxy groups.

Preferably, $R_b$ represents a hydrogen atom or a group selected from hydroxy and $C_1$-$C_4$ alkoxy groups.

Preferably, $R_c$ represents a hydrogen atom or a group selected from hydroxy and $C_1$-$C_4$ alkoxy groups.

Preferably, $R_3$ represents a halogen or a group selected from $C_1$-$C_3$ alkylamino, $C_1$-$C_3$ dialkylamino, or amine-($C_1$-$C_6$ alkyl)-amino groups.

More advantageously, $R_3$ represents a halogen or a group selected from amino, $C_1$-$C_2$ alkylamino, $C_1$-$C_2$ dialkylamino, amine-($C_1$-$C_3$ alkyl)amino or aminohexylamino groups.

More advantageously, $R_3$ represents a halogen or a group selected from $C_1$-$C_2$ alkylamino, $C_1$-$C_2$ dialkylamino, amine-($C_1$-$C_3$ alkyl)amino or aminohexylamino groups.

More preferably, $R_3$ is a chloro, amino, methylamino or aminoethylamino group and more preferably methylamino or aminoethylamino.

Advantageously, $R_3$ is an amino group of an α-amino acid or an amino group of an α-amino acid side chain.

In the case mentioned here, where $R_3$ is an amino acid, it is attached to the ring via the nitrogen of the α-aminated function of the α-amino acid or via the nitrogen of the α-amino acid sidechain amino function, for example, in the case of lysine.

Preferably, $R_a$ is selected from H, hydroxy and methoxy.
Preferably, $R_b$ is selected from H, hydroxy and methoxy.
Preferably, $R_c$ is selected from H, hydroxy and methoxy.

The present invention particularly relates to a compound characterized in that it has the formula (II):

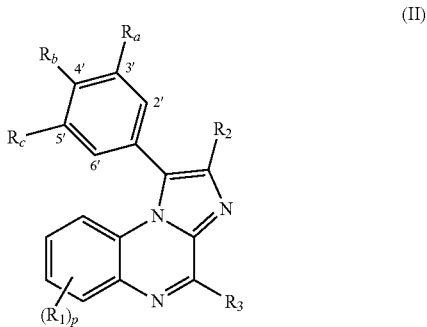

(II)

wherein the various $R_1$, $R_2$, $R_3$, $R_a$, $R_b$, $R_c$ and p groups are as defined above,
or a pharmaceutically acceptable salt thereof.

More particularly, the present invention relates to a compound having the formula (I) or (II) characterized in that:
$R_a$, $R_b$ and $R_c$ independently represent a hydrogen atom or a group selected from hydroxy or $C_1$-$C_4$ alkoxy groups, preferably a hydrogen atom or a hydroxy group,
or a pharmaceutically acceptable salt thereof.

An aspect of the present invention relates to a compound characterized in that it has the formula (III):

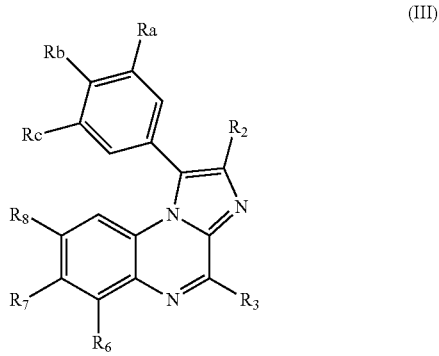

(III)

wherein the various $R_2$, $R_3$, $R_a$, $R_b$ and $R_c$ groups are as defined above,
$R_6$, $R_7$ and $R_8$ independently represent a hydrogen or halogen atom or a group selected from hydroxy, $C_1$-$C_4$ alkyl, $C_1$-$C_4$ alkoxy, amino, $C_1$-$C_4$ alkylamino, $C_1$-$C_4$ dialkylamino, cyano, $CF_3$, $OCF_3$, —$(CH_2)_nNR_4R_5$, —NH—$(CH_2)_nNR_4R_5$, —$(CH_2)_nCOR_4$, —$(CH_2)_nCO$—$NR_4R_5$, —$(CH_2)_nSO_2$—$NR_4R_5$, and —$(CH_2)_nCO_2R_4$ groups;
n being 0, 1, 2, 3 or 4, preferably n being 0; and
the various $R_4$ and $R_5$ independently represent a hydrogen atom or a $C_1$-$C_4$ alkyl group, preferably linear or branched;
or a pharmaceutically acceptable salt thereof.

Advantageously, the compound of the formula (III) is characterized in that:
$R_6$, $R_7$ and $R_8$ independently represent a hydrogen or halogen atom or a group selected from hydroxy, $C_1$-$C_4$ alkyl, $C_1$-$C_4$ alkoxy, $OCF_3$, preferably hydrogen, methoxy, $OCF_3$ or methyl groups;
or a pharmaceutically acceptable salt thereof.

In a particular embodiment, the present invention relates to a compound characterized in that it has the formula (IV):

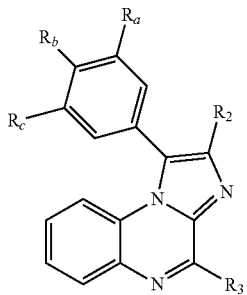

(IV)

wherein the various $R_2$, $R_3$, $R_a$, Rb and $R_c$ groups are as defined above;
or a pharmaceutically acceptable salt thereof.

In a particular embodiment, the invention is directed at a compound according to (I) or (II) wherein
$R_1$=H
$R_2$=H
$R_3$=$NH_2$ or $NHCH_3$
$R_a$ and $R_b$=OH and $R_c$=H In another particular embodiment, the invention is directed at a compound according to (I) or (II) wherein
$R_1$=H
$R_2$=H
$R_3$=$NH_2$ or $NHCH_3$
$R_a$ and $R_b$=$OCH_3$ and $R_c$=H Advantageously, the compounds according to the present invention are selected from the following compounds:

1. 1-(3,4-Dimethoxyphenyl)-N-methylimidazo[1,2-a]quinoxalin-4-amine
2. 1-(3,5-Dimethoxyphenyl)-N-methylimidazo[1,2-a]quinoxalin-4-amine
3. 1-(3,4-Dimethoxyphenyl)imidazo[1,2-a]quinoxalin-4-amine
4. N-Methyl-1-(3,4,5-trimethoxyphenyl)imidazo[1,2-a]quinoxalin-4-amine
5. 1-(3,4-Dihydroxyphenyl)imidazo[1,2-a]quinoxalin-4-amine
6. 1-(3,4-Dihydroxyphenyl)-N-methylimidazo[1,2-a]quinoxalin-4-amine
7. 1-(3,5-Dihydroxyphenyl)-N-methylimidazo[1,2-a]quinoxalin-4-amine
8. 4-(4-Amino-6-(trifluoromethyl)imidazo[1,2-a]quinoxalin-1-yl)benzene-1,2-diol
9. 4-(4-(Methylamino)-6-(trifluoromethyl)imidazo[1,2-a]quinoxalin-1-yl)benzene-1,2-diol
10. 4-(4-((2-Aminoethyl)amino)-6-(trifluoromethyl)imidazo[1,2-a]quinoxalin-1-yl)benzene-1,2-diol
11. 4-(4-((3-Aminopropyl)amino)-6-(trifluoromethyl)imidazo[1,2-a]quinoxalin-1-yl)benzene-1,2-diol
12. 4-(4-((6-Aminohexyl)amino)-6-(trifluoromethyl)imidazo[1,2-a]quinoxalin-1-yl)benzene-1,2-diol
13. 4-Amino-1-(3,4-dihydroxyphenyl)imidazo[1,2-a]quinoxaline-6-carbonitrile
14. 1-(3,4-Dihydroxyphenyl)-4-(methylamino)imidazo[1,2-a]quinoxaline-6-carbonitrile
15. 4-((2-Aminoethyl)amino)-1-(3,4-dihydroxyphenyl)imidazo[1,2-a]quinoxaline-6-carbonitrile
16. 4-((3-Aminopropyl)amino)-1-(3,4-dihydroxyphenyl)imidazo[1,2-a]quinoxaline-6-carbonitrile
17. 4-((6-Aminohexyl)amino)-1-(3,4-dihydroxyphenyl)imidazo[1,2-a]quinoxaline-6-carbonitrile
18. Methyl 4-amino-1-(3,4-dihydroxyphenyl)imidazo[1,2-a]quinoxaline-6-carboxylate
19. Methyl 1-(3,4-dihydroxyphenyl)-4-(methylamino)imidazo[1,2-a]quinoxaline-6-carboxylate
20. Methyl 4-((3-aminopropyl)amino)-1-(3,4-dihydroxyphenyl)imidazo[1,2-a]quinoxaline-6-carboxylate
21. Methyl 4-((6-aminohexyl)amino)-1-(3,4-dihydroxyphenyl)imidazo[1,2-a]quinoxaline-6-carboxylate
22. 4-Amino-1-(3,4-dihydroxyphenyl)imidazo[1,2-a]quinoxaline-6-carboxylic acid
23. 1-(3,4-Dihydroxyphenyl)-4-(methylamino)imidazo[1,2-a]quinoxaline-6-carboxylic acid
24. 4-((2-Aminoethyl)amino)-1-(3,4-dihydroxyphenyl)imidazo[1,2-a]quinoxaline-6-carboxylic acid
25. 4-((3-Aminopropyl)amino)-1-(3,4-dihydroxyphenyl)imidazo[1,2-a]quinoxaline-6-carboxylic acid
26. 4-((6-Aminohexyl)amino)-1-(3,4-dihydroxyphenyl)imidazo[1,2-a]quinoxaline-6-carboxylic acid
27. 4-(4,6-Diaminoimidazo[1,2-a]quinoxalin-1-yl)benzene-1,2-diol
28. 4-(6-Amino-4-(methylamino)imidazo[1,2-a]quinoxalin-1-yl)benzene-1,2-diol
29. 4-(6-Amino-4-((2-aminoethyl)amino)imidazo[1,2-a]quinoxalin-1-yl)benzene-1,2-diol
30. 4-(6-Amino-4-((3-aminopropyl)amino)imidazo[1,2-a]quinoxalin-1-yl)benzene-1,2-diol
31. 4-(6-Amino-4-((6-aminohexyl)amino)imidazo[1,2-a]quinoxalin-1-yl)benzene-1,2-diol
32. 4-(4-Amino-7-(trifluoromethyl)imidazo[1,2-a]quinoxalin-1-yl)benzene-1,2-diol
33. 4-(4-(Methylamino)-7-(trifluoromethyl)imidazo[1,2-a]quinoxalin-1-yl)benzene-1,2-diol
34. 4-(4-((2-Aminoethyl)amino)-7-(trifluoromethyl)imidazo[1,2-a]quinoxalin-1-yl)benzene-1,2-diol
35. 4-(4-((3-Aminopropyl)amino)-7-(trifluoromethyl)imidazo[1,2-a]quinoxalin-1-yl)benzene-1,2-diol
36. 4-(4-((6-Aminohexyl)amino)-7-(trifluoromethyl)imidazo[1,2-a]quinoxalin-1-yl)benzene-1,2-diol
37. 4-Amino-1-(3,4-dihydroxyphenyl)imidazo[1,2-a]quinoxaline-7-carbonitrile
38. 1-(3,4-Dihydroxyphenyl)-4-(methylamino)imidazo[1,2-a]quinoxaline-7-carbonitrile
39. 4-((2-Aminoethyl)amino)-1-(3,4-dihydroxyphenyl)imidazo[1,2-a]quinoxaline-7-carbonitrile
40. 4-((3-Aminopropyl)amino)-1-(3,4-dihydroxyphenyl)imidazo[1,2-a]quinoxaline-7-carbonitrile
41. 4-((6-Aminohexyl)amino)-1-(3,4-dihydroxyphenyl)imidazo[1,2-a]quinoxaline-7-carbonitrile
42. 4-Amino-1-(3,4-dihydroxyphenyl)imidazo[1,2-a]quinoxaline-7-carboxylic acid
43. 1-(3,4-Dihydroxyphenyl)-4-(methylamino)imidazo[1,2-a]quinoxaline-7-carboxylic acid
44. 4-((2-Aminoethyl)amino)-1-(3,4-dihydroxyphenyl)imidazo[1,2-a]quinoxaline-7-carboxylic acid
45. 4-((3-Aminopropyl)amino)-1-(3,4-dihydroxyphenyl)imidazo[1,2-a]quinoxaline-7-carboxylic acid
46. 4-((6-Aminohexyl)amino)-1-(3,4-dihydroxyphenyl)imidazo[1,2-a]quinoxaline-7-carboxylic acid
47. 4-(4,7-Diaminoimidazo[1,2-a]quinoxalin-1-yl)benzene-1,2-diol
48. 4-(7-Amino-4-(methylamino)imidazo[1,2-a]quinoxalin-1-yl)benzene-1,2-diol
49. 4-(7-Amino-4-((2-aminoethyl)amino)imidazo[1,2-a]quinoxalin-1-yl)benzene-1,2-diol 50. 4-(7-Amino-4-((3-aminopropyl)amino)imidazo[1,2-a]quinoxalin-1-yl)benzene-1,2-diol
51. 4-(7-Amino-4-((6-aminohexyl)amino)imidazo[1,2-a]quinoxalin-1-yl)benzene-1,2-diol
52. 4-(4-Amino-8-(trifluoromethyl)imidazo[1,2-a]quinoxalin-1-yl)benzene-1,2-diol
53. 4-(4-(Methylamino)-8-(trifluoromethyl)imidazo[1,2-a]quinoxalin-1-yl)benzene-1,2-diol
54. 4-(4-((2-Aminoethyl)amino)-8-(trifluoromethyl)imidazo[1,2-a]quinoxalin-1-yl)benzene-1,2-diol
55. 4-(4-((3-Aminopropyl)amino)-8-(trifluoromethyl)imidazo[1,2-a]quinoxalin-1-yl)benzene-1,2-diol
56. 4-(4-((6-Aminohexyl)amino)-8-(trifluoromethyl)imidazo[1,2-a]quinoxalin-1-yl)benzene-1,2-diol
57. 4-Amino-1-(3,4-dihydroxyphenyl)imidazo[1,2-a]quinoxaline-8-carbonitrile
58. 1-(3,4-Dihydroxyphenyl)-4-(methylamino)imidazo[1,2-a]quinoxaline-8-carbonitrile
59. 4-((2-Aminoethyl)amino)-1-(3,4-dihydroxyphenyl)imidazo[1,2-a]quinoxaline-8-carbonitrile
60. 4-((3-Aminopropyl)amino)-1-(3,4-dihydroxyphenyl)imidazo[1,2-a]quinoxaline-8-carbonitrile
61. 4-((6-Aminohexyl)amino)-1-(3,4-dihydroxyphenyl)imidazo[1,2-a]quinoxaline-8-carbonitrile
62. Methyl 4-amino-1-(3,4-dihydroxyphenyl)imidazo[1,2-a]quinoxaline-8-carboxylate
63. Methyl 1-(3,4-dihydroxyphenyl)-4-(methylamino)imidazo[1,2-a]quinoxaline-8-carboxylate
64. Methyl 4-((2-aminoethyl)amino)-1-(3,4-dihydroxyphenyl)imidazo[1,2-a]quinoxaline-8-carboxylate
65. Methyl 4-((3-aminopropyl)amino)-1-(3,4-dihydroxyphenyl)imidazo[1,2-a]quinoxaline-8-carboxylate
66. Methyl 4-((6-aminohexyl)amino)-1-(3,4-dihydroxyphenyl)imidazo[1,2-a]quinoxaline-8-carboxylate
67. 4-Amino-1-(3,4-dihydroxyphenyl)imidazo[1,2-a]quinoxaline-8-carboxylic acid
68. 1-(3,4-Dihydroxyphenyl)-4-(methylamino)imidazo[1,2-a]quinoxaline-8-carboxylic acid
69. 4-((2-Aminoethyl)amino)-1-(3,4-dihydroxyphenyl)imidazo[1,2-a]quinoxaline-8-carboxylic acid
70. 4-((3-Aminopropyl)amino)-1-(3,4-dihydroxyphenyl)imidazo[1,2-a]quinoxaline-8-carboxylic acid
71. 4-((6-Aminohexyl)amino)-1-(3,4-dihydroxyphenyl)imidazo[1,2-a]quinoxaline-8-carboxylic acid
72. 4-(4,8-Diaminoimidazo[1,2-a]quinoxalin-1-yl)benzene-1,2-diol
73. 4-(8-Amino-4-(methylamino)imidazo[1,2-a]quinoxalin-1-yl)benzene-1,2-diol
74. 4-(8-Amino-4-((2-aminoethyl)amino)imidazo[1,2-a]quinoxalin-1-yl)benzene-1,2-diol
75. 4-(8-Amino-4-((3-aminopropyl)amino)imidazo[1,2-a]quinoxalin-1-yl)benzene-1,2-diol
76. 4-(8-Amino-4-((6-aminohexyl)amino)imidazo[1,2-a]quinoxalin-1-yl)benzene-1,2-diol
77. tert-Butyl (2-((1-(3,4-dimethoxyphenyl)imidazo[1,2-a]quinoxalin-4-yl)amino)ethyl)carbamate
78. tert-Butyl (6-((1-(3,4-dimethoxyphenyl)imidazo[1,2-a]quinoxalin-4-yl)amino)hexyl)carbamate
79. tert-Butyl 4-(1-(3,4-dimethoxyphenyl)imidazo[1,2-a]quinoxalin-4-yl)piperazine-1-carboxylate
80. tert-Butyl (3-((1-(3,4-dimethoxyphenyl)imidazo[1,2-a]quinoxalin-4-yl)amino)propyl)carbamate
81. N-(1,3-Dihydroxy-2-(hydroxymethyl)propan-2-yl)-2-((1-(3,4-dimethoxyphenyl) imidazo[1,2-a]quinoxalin-4-yl)amino)acetamide
82. 1-(3,4-Dimethoxyphenyl)-N-methyl-7-(trifluoromethyl)imidazo[1,2-a]quinoxalin-4-amine
83. 1-(3,4-Dimethoxyphenyl)-N-methyl-7-(trifluoromethoxy)imidazo[1,2-a]quinoxalin-4-amine
84. 1-(3,4-Dimethoxyphenyl)-N-methyl-7-(carbonitrile)imidazo[1,2-a]quinoxalin-4-amine
85. 1-(3,4-Dimethoxyphenyl)-N-methyl-8-(trifluoromethyl)imidazo[1,2-a]quinoxalin-4-amine
86. 1-(3,4-Dihydroxyphenyl)imidazo[1,2-a]quinoxalin-4-amine
87. 1-(3,4-Dihydroxyphenyl)-N-methylimidazo[1,2-a]quinoxalin-4-amine
88. 1-(3,5-Dihydroxyphenyl)-N-methylimidazo[1,2-a]quinoxalin-4-amine
89. 4-(4-((2-Aminoethyl)amino)imidazo[1,2-a]quinoxalin-1-yl)benzene-1,2-diol
90. 2-((1-(3,4-Dihydroxyphenyl)imidazo[1,2-a]quinoxalin-4-yl)amino)ethylammonium chloride
91. 4-(4-((6-Aminohexyl)amino)imidazo[1,2-a]quinoxalin-1-yl)benzene-1,2-diol
92. 6-((1-(3,4-Dihydroxyphenyl)imidazo[1,2-a]quinoxalin-4-yl)amino)hexan-1-ammonium chloride
93. 4-(4-(Piperazin-1-yl)imidazo[1,2-a]quinoxalin-1-yl)benzene-1,2-diol
94. 4-(4-((3-Aminopropyl)amino)imidazo[1,2-a]quinoxalin-1-yl)benzene-1,2-diol
95. N-(1,3-Dihydroxy-2-(hydroxymethyl)propan-2-yl)-2-((1-(3,4-dihydroxyphenyl)imidazo[1,2-a]quinoxalin-4-yl)amino)acetamide
96. 4-(4-(Methylamino)-7-(trifluoromethoxy)imidazo[1,2-a]quinoxalin-1-yl)benzene-1,2-diol
97. 4-(4-(Methylamino)-8-(trifluoromethyl)imidazo[1,2-a]quinoxalin-1-yl)benzene-1,2-diol
98. (2S)-(2)-2-((1-(3,4-Dimethoxyphenyl)imidazo[1,2-a]quinoxalin-4-yl)amino)propanoic acid
99. (2S)-2-((1-(3,4-Dimethoxyphenyl)imidazo[1,2-a]quinoxalin-4-yl)amino)-3-methylbutanoic acid
100. (2S)-2-Amino-5-((1-(3,4-dihydroxyphenyl)imidazo[1,2-a]quinoxalin-4-yl)amino)pentanoic acid Advantageously, the compound of the formula (I), (II), (III) or (IV) is characterized in that:
$R_2$ and $R_c$ are hydrogen atoms;
$R_3$ is a methylamino or amine group and
$R_a$ and $R_b$ are hydroxy groups;
or a pharmaceutically acceptable salt thereof.

Advantageously, the compound according to the present invention may be selected from the group consisting of 1-(3,4-dimethoxyphenyl)-N-methylimidazo[1,2-a]quinoxalin-4-amine, 1-(3,5-dimethoxyphenyl)-N-methylimidazo[1,2-a]quinoxalin-4-amine, 1-(3,4-dimethoxyphenyl)imidazo[1,2-a]quinoxalin-4-amine, 1-(3,5-dimethoxyphenyl)imidazo[1,2-a]quinoxalin-4-amine, 1-(3,4,5-trimethoxyphenyl)-N-methylimidazo[1,2-a]quinoxalin-4-amine, 1-(3,4-dihydroxyphenyl)-N-methylimidazo[1,2-a]quinoxalin-4-amine, 1-(3,4-dihydroxyphenyl)imidazo[1,2-a]quinoxalin-4-amine, 1-(3,5-dihydroxyphenyl)-N-methylimidazo[1,2-a]quinoxalin-4-amine and 1-(3,5-dihydroxyphenyl)imidazo[1,2-a]quinoxalin-4-amine.

Furthermore, the composition according to the present invention can be formulated for administration to mammals, including humans. The dosing regimen varies according to the treatment and the affection in question. These compositions are designed for administration via the digestive tract or the parenteral tract.

In the pharmaceutical compositions of the present invention for oral, sublingual, subcutaneous, intramuscular, intravenous, transdermal, local or rectal administration, the active ingredient can be administered in unit dose forms of administration, mixed with conventional pharmaceutical supports, in animals or in human beings. Suitable unit dose forms of administration include forms by oral route such as tablets, gelatin capsules, powders, granules and oral solutions or suspensions, forms for sublingual and buccal administration, forms for subcutaneous, intramuscular, intravenous, intranasal or intraocular administration and forms for rectal administration.

The present invention also relates to a compound as described herein for use in the treatment of a solid cancer or a liquid cancer, optionally metastatic or secondary.

Advantageously, the compound for use according to the present invention is characterized in that the cancer is a cancer of the breast, prostate, pancreas, lungs, esophagus, skin, bladder, stomach, liver, uterus, colon or rectum.

In a particular embodiment, the compound for use according to the present invention is characterized in that the cancer is a metastatic prostate cancer. Metastatic prostate cancers are cancers that produce metastases, i.e., tumors formed from cancer cells that have detached from a primary tumor and have migrated via the lymph or blood vessels into another part of the body where they become established and develop.

Equally advantageously, the compound for use according to the present invention is characterized in that the cancer is a cancer of the blood or of certain blood cells such as lymphocytes or leukocytes.

Medicinal Chemistry 16, 6601-6610; Masquefa et al. 2009 European Journal of Medicinal Chemistry 44, 3406-3411). The advantage of this synthesis scheme is direct production of imidazoquinoxaline-structured compounds with no intermediate or final purification. This synthesis strategy makes it possible to obtain the compound 3 with good yields and sufficient purity to continue the synthesis (scheme 1). The production of derivatives substituted at the 4-position by a chlorine atom or an amine function may benefit from microwave assistance, although conventional heating is always an option. The use of microwaves makes it possible to decrease reaction times and to optimize reaction yields. The Suzuki-type cross-coupling reaction may also be carried out under microwave assistance and makes it possible to obtain a great diversity of new derivatives substituted at the 1-position of the heterocycle. The retrosynthesis scheme 1 illustrates the cyclization method preferably used to obtain a carbonyl-imidazol dimer 1 by bimolecular condensation of 2-imidazol carboxylic acid. The carbonyl-imidazol dimer 1 is coupled to an ortho-fluoroaniline to give an intermediate 2, which is then cyclized to provide the tricyclic compounds 3. Chlorinated compounds are obtained by reaction of phosphorus oxychloride in the presence of N,N-diethylaniline in a sealed flask under microwave assistance then purified by liquid chromatography on silica gel column.

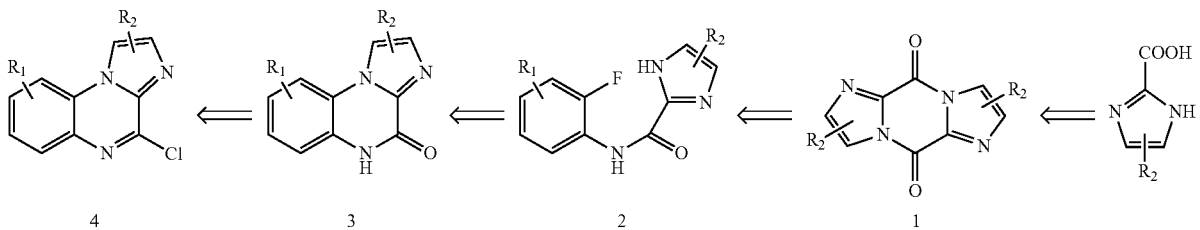

4   3   2   1

Moreover, the compound for use according to the present invention is characterized in that the cancer is a melanoma, a cancer of the pancreas, colon or prostate, a lymphoma, a leukemia or a myeloma.

FIGURES

FIG. 1. Study of the innovative effect of compounds of the selection patent on the polymerization of purified tubulin. This is a comparative study of the effect on the polymerization of purified tubulin by compounds of the selection patent compared to that of the compounds of the patent FR 2,921,927. Polymerized tubulin absorbs at 350 nm. EAPB0503 decreases the absorbance level, unlike EAPB02303 which leaves it unchanged.

EXAMPLES

The following examples in no way limit the subject matter of the present invention and are provided for purposes of illustrating the present invention.

General Synthesis of Imidazo[1,2-a]quinoxaline Compounds

Imidazoquinoxaline derivatives unsubstituted at the 1-position are synthesized according to a synthesis strategy described previously (Moarbess et al. 2008 Bioorganic &

Schema 1. Retrosynthesis of Intermediate Chlorinated Imidazoquinoxaline Compounds.

The chlorine atom at the 4-position is substituted by a suitable group ($R_3$). The compounds thus substituted at the 4-position of the heterocycle are treated with N-bromosuccinimide under microwave assistance to obtain the new derivatives substituted at the 1- or 2-position by a bromine atom.

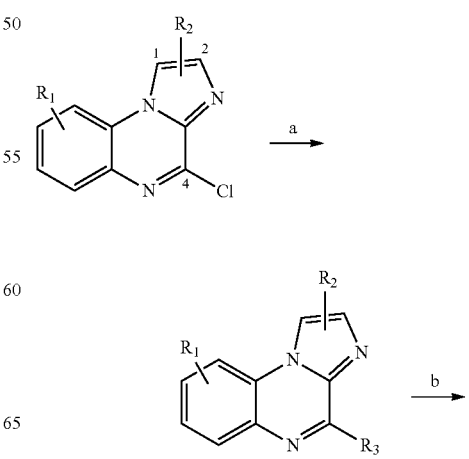

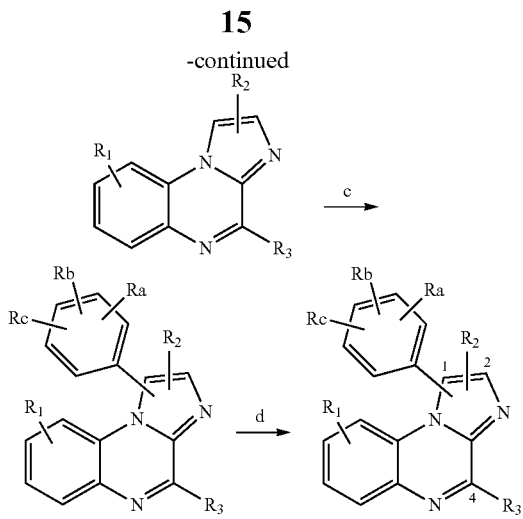

Schema 2: Synthesis of Imiqualine Derivatives: a) EtOH, Ammonia or Suitable Amine, MW (150° C., 20 min); (b) NBS, CHCl$_3$, reflux, 1 h30 min; c) Suitable Arylboronic Acid ([Ph(R$_a$,R$_b$,R$_c$)]—B(OH)$_2$), Pd(PPh$_3$)$_4$, Na$_2$CO$_3$, DME/H$_2$O (2/1), MW (140° C., 20 min); d) BBr$_3$, CH$_2$Cl$_2$, 1 h30 min, RT.

The arylboronic acids are coupled by Suzuki reaction under palladium catalysis with the brominated imidazoquinoxaline derivatives at the 1- or 2-position to obtain the substituted aryl compounds with good yields. If methoxylated aryl compounds are used for this coupling step, demethylation can be used to regenerate the phenol functions under the action of boron tribromide.

EXPERIMENTAL SECTION

Chemistry

Solvents and reagents are obtained from commercial sources and are used without further purification. $^1$H and $^{13}$C NMR spectra are recorded on a Brüker AC 400 spectrometer. Chemical shifts are expressed in parts per million (ppm) with as reference the resonance of tetramethylsilane in the deuterated analysis solvent. Coupling constants are expressed in hertz (Hz), with the following coupling characteristics: (s) singlet, (br s) broad singlet, (d) doublet, (dd) doublet of doublets (t), triplet, (td) triplet of doublets, (m) multiplet. Silica column chromatographies are carried out with Aldrich silica gel 60 Å (230-400 mesh). Elemental analyses are carried out at the Central Microanalysis Department (Montpellier, France). Spectrometry analyses are obtained by a Micromass-QTOF spectrometer (Waters) equipped with an ESI source. The data are recorded in positive mode between 50 and 1500 Da. The capillary and cone voltages are 3000V and 20V, respectively. Microwave assistance is provided by means of a Biotage Initiator (France) device.

Procedure for Addition at the 4-Position

Procedure for Addition of Ammonia

Imidazo[1,2-a]quinoxalin-4-amine

A 33% aqueous ammonia solution (2.7 mL, 19.7 mmol) is added to a solution of 4-chloroimidazo[1,2-a]quinoxaline (0.500 g, 2.5 mmol) in acetonitrile (5 mL). The mixture is heated by microwaves to 140° C. for 4 hours. The solvent is evaporated under reduced pressure and the residue is dissolved in 20 mL of dichloromethane. This solution is successively washed with saturated NaCl solution (15 mL) and water (15 mL), dried (Na$_2$SO$_4$), and concentrated under reduced pressure. The product obtained (94% yield) is used without further purification. $^1$H NMR (300 MHz, DMSO-d$_6$) δ: 7.92 (d, 1H), 7.79 (d, 1H), 7.72 (m, 2H), 7.65 (m, 2H), 6.66 (br s, 2H); $^{13}$C (300 MHz, DMSO-d$_6$) δ: 142.49, 131.92, 129.26, 128.88, 127.58, 125.81, 125.26, 124.72, 114.26, 111.75.

Procedure for Addition of Methylamine

4-Chloroimidazo[1,2-a]quinoxaline is placed in solution in ethanol in a vial suitable for microwave-assisted reactions and equipped with a magnetic stirring bar. A solution of 33% methylamine in ethanol is added (20 eq.). The mixture is sealed and then homogenized ultrasonically before being placed under microwaves for 20 min at 150° C. The power delivered is automatically adjusted to about 50 watts. The ethanol is evaporated under reduced pressure. The reaction medium is taken up in dichloromethane, washed three times with saturated sodium bicarbonate solution, dried over magnesium sulfate, filtered and concentrated. The crude reaction product is purified by column chromatography on silica gel in order to obtain the expected products.

N-Methylimidazo[1,2-a]quinoxalin-4-amine (PED26)

Addition of methylamine on 4-chloroimidazo[1,2-a]quinoxaline. Yield 88%. Mw: 198.22 g/mol. $^1$H-NMR δ (ppm, 400 MHz, DMSO d6) 3.25 (d, 3H, NHCH3), 6.15 (s, 1H), 7.25 (t, 1H), 7.40 (t, 1H), 7.52 (s, 1H), 7.65 (dd, 1H), 7.75 (dd, 1H), 7.92 (s, 1H). $^{13}$C (300 MHz, DMSO-d$_6$) δ: 29.20, 113.89, 114.14, 124.34, 125.14, 127.20, 128.17, 129.40, 131.99, 139.17, 142.25

N-Methyl-7-(trifluoromethyl)imidazo[1,2-a]quinoxalin-4-amine

Addition of methylamine on 4-chloro-7-(trifluoromethyl) imidazo[1,2-a]quinoxaline. Yield: 94%. Mw: 266.22 g/mol. 1H-NMR δ (ppm, 400 MHz, DMSO d6) 3.04 (d, 3H, CH3NH, J=8 Hz), 7.60 (d, 1H, CH 8, J=8 Hz), 7.67 (d, 1H, CH 2, J=4 Hz), 7.85 (s, 1H, CH 6), 8.06 (d, 1H, NHCH3, J=4 Hz), 8.31 (d, 1H, CH 9, J=8 Hz), 8.69 (d, 1H, CH 1, J=4 Hz). 13C-NMR δ (ppm, 100 MHz, DMSO d6) 27.73 (CH3NH), 115.71 (CH 1), 117.15 (CH 9), 118.92 (CH 8), 123.22 (CH 6), 127.26 (Cq 5'), 132.76 (CH 2), 132.87 (Cq 3'), 137.63 (Cq 9'), 149.11 (Cq 4). 19F-NMR δ (ppm, 400 MHz, DMSO d6) −60.42. MS (ESI +, QTof, m/z): 267.10 [M+H]$^+$ N-Methyl-7-(trifluoromethoxy)imidazo[1,2-a]quinoxalin-4-amine Addition of methylamine on 4-chloro-7-(trifluoromethoxy)imidazo[1,2-a]quinoxaline. Yield: 70%. Mw: 282.22 g/mol. 1H-NMR δ (ppm, 400 MHz, DMSO d6) 3.04 (d, 3H, CH3NH, J=8 Hz), 7.28 (d, 1H, CH 8, J=8 Hz), 7.49 (s, 1H, CH 6), 7.64 (d, 1H, CH 2, J=4 Hz), 8.02 (d, 1H, NHCH3, J=4 Hz), 8.21 (d, 1H, CH 9, J=8 Hz), 8.62 (d, 1H, CH 1, J=4 Hz). 13C-NMR δ (ppm, 100 MHz, DMSO d6) 27.73 (CH3NH), 115.51 (CH 1, CH 8), 117.49 (CH 9), 117.99 (CH 6), 123.79 (Cq 5'), 132.51 (CH 2), 132.84 (Cq 3'), 138.75 (Cq 9'), 146.71 (Cq 7), 149.06 (Cq 4). 19F-NMR δ (ppm, 100 MHz, DMSO d6) −56.81 (OCF3). MS (ESI +, QTof, m/z): 282.9 [M+H]$^+$

N-Methyl 7-(carbonitrile)imidazo[1,2-a]quinoxalin-4-amine

Addition of methylamine on 4-chloro-7-(carbonitrile)imidazo[1,2-a]quinoxaline. Yield: 60%. Mw: 223.23 g/mol. 1H-NMR δ (ppm, 400 MHz, DMSO d6) 3.04 (d, 3H, CH3NH), 7.68 (s, 1H, CH 2), 7.70 (d, 1H, CH 8, J=8 Hz), 8.00 (s, 1H, CH 6), 8.11 (m, 1H, NHCH3), 8.28 (d, 1H, CH 9, J=8 Hz), 8.68 (s, 1H, CH 1). 13C-NMR δ (ppm, 100 MHz, DMSO d6) 27.77 (CH3), 109.23 (Cq 7), 115.83 (CH1), 117.40 (CH 9), 119.25 (Cq CN), 125.76 (CH 8), 127.94 (Cq 5'), 130.39 (CH 6), 132.93 (CH 2), 133.13 (Cq 3'), 137.79 (Cq 9'), 149.10 (Cq 4). MS (ESI +, QTof, m/z): 224.0 [M+H]$^+$

N-Methyl-8-(trifluoromethyl)imidazo[1,2-a]quinoxalin-4-amine

Addition of methylamine on 4-chloro-8-(trifluoromethyl)imidazo[1,2-a]quinoxaline. Yield: 82%. Mw: 266.22 g/mol. 1H-NMR δ (ppm, 400 MHz, DMSO d6) 3.06 (d, 3H, CH3NH, J=4 Hz), 7.65 (d, 1H, CH 2, 4 Hz), 7.67 (d, 1H, CH 7, J=8 Hz), 7.72 (d, 1H, CH 6, J=8 Hz), 8.15 (m, 1H, NH), 8.55 (s, 1H, CH 9), 8.81 (s, 1H, CH 1). 13C-NMR δ (ppm, 100 MHz, DMSO d6) 27.75 (CH3NH), 113.72 (CH 9), 115.88 (CH 1), 122.46 (CH 7), 124.90 (Cq 5'), 127.08 (CH 6), 132.57 (CH 2), 132.95 (Cq 3'), 140.53 (Cq 9'), 149.49 (Cq 4). 19F-NMR δ (ppm, 100 MHz, DMSO d6) −59.36 (CF3). MS (ESI +, QTof, m/z): 267.00 [M+H]$^+$

Procedure for Addition of Another Primary or Secondary Amine

4-Chloroimidazo[1,2-a]quinoxaline and the primary (or secondary) amine (2 eq.) are solubilized in acetonitrile (12 mL) in a vial suitable for microwave-assisted reactions and equipped with a magnetic stirring bar. DIEA (4 eq.) is added. The mixture is sealed and then homogenized ultrasonically before being placed under microwaves for 20 min at 150° C. The power delivered is adjusted automatically to about 45 watts. The acetonitrile is evaporated under reduced pressure. The reaction medium is taken up in ethyl acetate, washed with saturated ammonium chloride solution, then with distilled water, and finally with saturated sodium chloride solution. The organic phase is dried over magnesium sulfate, filtered and concentrated. The crude reaction product is purified by column chromatography on silica gel in order to obtain the expected addition compound.

tert-Butyl (2-(imidazo[1,2-a]quinoxalin-4-ylamino)ethyl)carbamate

Addition of N-Boc-ethylenediamine on 4-chloro-imidazo[1,2-a]quinoxaline. Yield: 81%. Mw: 327.38 g/mol. 1H-NMR δ (ppm, 400 MHz, DMSO d6) 1.36 (s, 9H, 3×CH3 tBu), 3.26 (qd, 2H, CH2NHBoc, J=4 Hz), 3.61 (qd, 2H, CH2NH, J=4 Hz), 7.01 (t, 1H, NHBoc, J=4 Hz), 7.28 (t, 1H, CH 7, J=8 Hz), 7.30 (t, 1H, CH 8, J=8-Hz), 7.58 (d, 1H, CH 9, J=8 Hz), 7.62 (d, 1H, CH 2, J=4 Hz), 7.68 (t, 1H, NH, J=4 Hz), 8.11 (d, 1H, CH 6, J=8 Hz), 8.60 (d, 1H, CH 1, J=4 Hz). 13C-NMR δ (ppm, 100 MHz, DMSO d6) 28.68 (CH3 tBu), 40.00 (CH2NHBoc, CH2NH), 78.07 (Cq tBu), 115.03 (CH 1), 115.83 (CH 6), 123.17 (CH 7), 124.77 (Cq 5'), 126.62 (CH 9), 126.78 (CH 8), 132.26 (CH 2), 132.45 (Cq 3'), 137.17 (Cq 9'), 147.79 (Cq 4), 156.23 (C=O carbamate). MS (ESI +, QTof, m/z): 328.18 [M+H]$^+$ tert-Butyl (6-(imidazo[1,2-a]quinoxalin-4-ylamino)hexyl)carbamate

Addition of NBoc-1,6-hexanediamine on 4-chloroimidazo[1,2-a]quinoxaline. Yield: 89%. Mw: 383.49 g/mol. 1H-NMR δ (ppm, 400 MHz, DMSO d6) 1.29 to 1.40 (m, 15H, 3×CH3 tBu, CH2CH2CH2NH, CH2CH2CH2NHBoc, CH2CH2NHBoc), 1.64 (qt, 2H, CH2CH2NH, J=8 Hz), 2.91 (qd, 2H, CH2NHBoc, J=4 Hz), 3.56 (qd, 2H, CH2NH, J=4 Hz), 6.76 (t, 1H, NHBoc, J=4 Hz), 7.27 (t, 1H, CH 7, J=8 Hz), 7.37 (t, 1H, CH 8, J=8 Hz), 7.57 (d, 1H, CH 9, J=8 Hz), 7.61 (d, 1H, CH 2, J=4 Hz), 7.68 (t, 1H, NH, J=4 Hz), 8.07 (d, 1H, CH 6, J=8 Hz), 8.58 (d, 1H, CH 1, J=4 Hz). 13C-NMR δ (ppm, 100 MHz, DMSO d6) 26.55 and 26.73 (CH2CH2CH2NH, CH2CH2CH2NHBoc), 28.73 (CH3 tBu), 29.24 (CH2CH2NH), 29.95 (CH2CH2NHBoc), 40.00 (CH2NHBoc, CH2NH), 77.73 (Cq tBu), 114.96 (CH 1), 115.78 (CH 6), 122.88 (CH 7), 124.66 (Cq 5'), 126.59 (CH 9), 126.74 (CH 8), 132.15 (CH 2), 132.93 (Cq 3'), 137.42 (Cq 9'), 147.74 (Cq 4), 156.04 (C=O carbamate). MS (ESI +, QTof, m/z): 384.24 [M+H]$^+$ tert-Butyl 4-(imidazo[1,2-a]quinoxalin-4-yl)piperazine-1-carboxylate

Addition of 1-Boc-piperazine on 4-chloroimidazo[1,2-a]quinoxaline. Yield: 63%. Mw: 353.42 g/mol. 1H-NMR δ (ppm, 400 MHz, DMSO d6) 1.44 (s, 9H, 3×CH3 tBu), 3.51 (m, 4H, 2×CH2NBoc), 4.30 (m, 4H, 2×CH2NC=N), 7.33 (t, 1H, CH 7, J=8 Hz), 7.44 (t, 1H, CH 8, J=8 Hz), 7.60 (d, 1H, CH 9, J=8 Hz), 7.69 (d, 1H, CH 2, J=4 Hz), 8.14 (d, 1H, CH 6, J=8 Hz), 8.68 (d, 1H, CH 1, J=4 Hz). 13C-NMR δ (ppm, 100 MHz, DMSO d6) 28.54 (CH3 tBu), 44.5 (CH2NBoc), 46.06 (CH2NC=N), 79.52 (Cq tBu), 114.82 (CH 1), 115.67 (CH 6), 124.01 (CH 7), 124.98 (Cq 5'), 126.97 (CH 9, CH 8), 136.03 (CH 2), 132.52 (Cq 3'), 136.03 (Cq 9'), 147.53 (Cq 4), 154.44 (C=O carbamate). MS (ESI +, QTof, m/z): 354.19 [M+H]$^+$ tert-Butyl (3-(imidazo[1,2-a]quinoxalin-4-ylamino)propyl)carbamate

Addition of NBoc-1,3-diaminopropane on 4-chloroimidazo[1,2-a]quinoxaline. Yield: 93%. Mw: 341.41 g/mol. 1H-NMR δ (ppm, 400 MHz, DMSO d6) 1.37 (s, 9H, 3×CH3 tBu), 1.74 (m, 2H, CH2CH2NHBoc), 3.02 (qd, 2H, CH2NHBoc, J=4 Hz), 3.56 (qd, 2H, CH2NH, J=4 Hz), 6.93 (t, 1H, NHBoc, J=4 Hz), 7.26 (t, 1H, CH 7, J=8 Hz), 7.37 (t, 1H, CH 8, J=8 Hz), 7.58 (d, 1H, CH 9, J=8 Hz), 7.60 (s, 1H, CH 2, J=4 Hz), 7.70 (t, 1H, NH, J=4 Hz), 8.08 (d, 1H, CH 6, J=8 Hz), 8.59 (s, 1H, CH 1, J=4 Hz). 13C-NMR δ (ppm, 100 MHz, DMSO d6) 28.72 (CH3 tBu), 29.77 (CH2CH2NHBoc), 37.76 (CH2NH), 37.94 (CH2NHBoc), 77.92 (Cq tBu), 115.04 (CH 1), 115.83 (CH 6), 123.03 (CH 7), 124.70 (Cq 5'), 126.50 (CH 9), 126.76 (CH 8), 132.23 (CH 2), 132.53 (Cq 3'), 137.26 (Cq 9'), 147.79 (Cq 4), 156.11 (C=O carbamate). MS (ESI +, QTof, m/z): 342.19 [M+H]$^+$

2-(Acetoxymethyl)-2-(2-(imidazo[1,2-a]quinoxalin-4-ylamino)acetamido)propane-1,3-diyl diacetate Addition of 2-(acetoxymethyl)-2-(2-aminoacetamido)propane-1,3-diyl diacetate on 4-chloroimidazo[1,2-c]quinoxaline. Yield: 44%. Mw: 471.46 g/mol. 1H-NMR δ (ppm, 400 MHz, DMSO d6) 1.95 (s, 6H, 3×CH2OAc), 4.14 (d, 2H, CH2 Gly, J=8 Hz), 4.30 (s, 9H, 3×COCH3), 7.32 (t, 1H, CH 7, J=8 Hz), 7.42 (t, 1H, CH 8, J=8 Hz), 7.56 (d, 1H, CH 9, J=8 Hz), 7.60 (d, 1H, CH 2, J=4 Hz), 7.66 (t, 1H, NH, J=4 Hz), 8.00 (s, 1H, NH), 8.12 (d, 1H, CH 6, J=8 Hz), 8.64 (s, 1H, CH 1, J=4 Hz). 13C-NMR δ (ppm, 100 MHz, DMSO d6) 20.92 (CH2OAc), 44.15 (CH2 Gly), 57.41 (Cq Tris), 62.35 (COCH3), 115.18 (CH 1), 115.94 (CH 6), 123.64 (CH 7), 124.98 (Cq 5'), 126.66 (CH 9), 126.86 (CH 8), 132.53 (CH 2), 132.63 (Cq 3'), 136.84 (Cq 9'), 147.46 (Cq 4), 170.24 (C=O amide), 170.46 (3×C=O ester). MS (ESI +, QTof, m/z): 472.18 [M+H]+

Procedure for Addition of an Amine Function of an α-Amino Acid

4-Chloroimidazo[1,2-a]quinoxaline, amino acid (4 eq.) and diisopropylethylamine (4 eq.) are solubilized in dimethylformamide (12 mL) in a vial suitable for microwave-assisted reactions and equipped with a magnetic stirring bar. The mixture is sealed and then homogenized ultrasonically before being placed under microwaves for 20 min at 150° C. The power delivered is adjusted automatically to about 45 watts. The dimethylformamide is evaporated under reduced pressure. The reaction medium is taken up in ethyl acetate, washed with saturated ammonium chloride solution, then with distilled water, and finally with saturated sodium chloride solution. The organic phase is dried over magnesium sulfate, filtered and concentrated. The crude reaction product is purified by column chromatography on silica gel in order to obtain the expected addition compound.

tert-Butyl 2-(imidazo[1,2-a]quinoxalin-4-ylamino) acetate

Yield: 42%. Mw: 298.34 g/mol. 1H-NMR δ (ppm, 400 MHz, DMSO d6) 1.42 (s, 9H, 3×CH3 tBu), 4.12 (d, 2H, CH2 Gly, J=8 Hz), 7.31 (t, 1H, CH 7, J=8 Hz), 7.35 (t, 1H, CH 8, J=8 Hz), 7.52 (t, 1H, CH 9, J=8 Hz), 7.66 (s, 1H, CH 2), 7.95 (t, 1H, NH, J=8 Hz), 8.14 (d, 1H, CH 6, J=8 Hz), 8.64 (s, 1H, CH 1). MS (ESI +, QTof, m/z): 299.0 [M+H]+

General Bromination Procedure

The compound derived from the addition of an amine at the 4-position and N-bromosuccinimide (1.3 eq.) are solubilized in chloroform at room temperature and with stirring. The reaction medium is heated at reflux for 1 h 30 m. After returning to room temperature, 5% aqueous sodium bicarbonate solution is added to the reaction medium. The aqueous phase is extracted three times with dichloromethane. The organic phases are combined, dried over sodium sulfate, filtered and concentrated under reduced pressure. The product obtained is used without further purification; the reaction is quantitative.

1-Bromoimidazo[1,2-a]quinoxalin-4-amine

Mw: 263.09 g/mol. 1H NMR (300 MHz, DMSO-d6) δ: 7.95 (d, 1H), 7.75 (m, 2H), 7.71 (m, 1H), 7.68 (m, 1H), 6.65 (br s, 2H); 13C (300 MHz, DMSO-d6) δ: 142.20, 138.78, 129.66, 128.16, 127.17, 126.95, 126.18, 125.51, 113.98, 99.27.

1-Bromo-N-methylimidazo[1,2-a]quinoxalin-4-amine (CPA8)

Mw: 277.12 g/mol. 1H NMR (300 MHz, DMSO-d6) δ: 3.25 (d, 3H), 6.15 (s, 1H), 7.25 (t, 1H), 7.40 (t, 1H), 7.65 (dd, 1H), 7.75 (dd, 1H), 9.10 (s, 1H). 13C (300 MHz, DMSO-d6) δ: 29.20, 101.40, 113.86, 125.13, 126.03, 127.09, 127.78, 128.96, 138.85, 140.54, 141.97.

tert-Butyl (2-((1-bromoimidazo[1,2-a]quinoxalin-4-yl)amino)ethyl)carbamate

Mw: 406.28 g/mol. 1H-NMR δ (ppm, 400 MHz, DMSO d6) 1.36 (s, 9H, 3×CH3 tBu), 3.26 (m, 2H, CH2NHBoc), 3.59 (m, 2H, CH2NH), 6.98 (m, 1H, NHBoc), 7.30 (t, 1H, CH 7, J=8 Hz), 7.35 (t, 1H, CH 8, J=8 Hz), 7.61 (d, 1H, CH 9, J=8 Hz), 7.72 (m, 2H, CH 2, NH), 8.96 (d, 1H, CH 6, J=8 Hz). 13C-NMR δ (ppm, 100 MHz, DMSO d6) 28.68 (CH3 tBu), 40.00 (CH2NHBoc, CH2NH), 78.09 (Cq tBu), 99.35 (Cq 1), 114.98 (CH 6), 122.66 (CH 7), 125.91 (Cq 5'), 127.34 (CH 8, CH 9), 134.20 (CH 2), 134.35 (Cq 3'), 138.03 (Cq 9'), 147.35 (Cq 4), 156.24 (C=O carbamate). MS (ESI +, QTof, m/z): 406.08 [M+H]+ tert-Butyl (6-((1-bromoimidazo[1,2-a]quinoxalin-4-yl)amino)hexyl)carbamate

Mw: 462.38 g/mol. 1H-NMR δ (ppm, 400 MHz, DMSO d6) 1.29 to 1.40 (m, 15H, 3×CH3 tBu, CH2CH2CH2NH, CH2CH2CH2NHBoc, CH2CH2NHBoc), 1.63 (m, 2H, CH2CH2NH), 2.87 (qd, 2H, CH2NHBoc, J=4 Hz), 3.51 (qd, 2H, CH2NH, J=4 Hz), 6.76 (t, 1H, NHBoc, J=4 Hz), 7.28 (t, 1H, CH 7, J=8 Hz), 7.42 (t, 1H, CH 8, J=8 Hz), 7.58 (d, 1H, CH 9, J=8 Hz), 7.63 (s, 1H, CH 2), 7.74 (m, 1H, NH), 8.94 (d, 1H, CH 6, J=8 Hz). 13C-NMR δ (ppm, 100 MHz, DMSO d6) 26.53 and 26.69 (CH2CH2CH2NH, CH2CH2CH2NHBoc), 28.73 (CH3 tBu), 29.14 (CH2CH2NH), 29.93 (CH2CH2NHBoc), 40.00 (CH2NHBoc, CH2NH), 77.73 (Cq tBu), 99.39 (Cq 1), 114.96 (CH 6), 122.45 (CH 7), 125.73 (Cq 5'), 127.31 (CH 8, CH 9), 134.20 (Cq 3'), 134.50 (CH 2), 134.64 (Cq 9'), 149.14 (Cq 4), 156.03 (C=O carbamate). MS (ESI +, QTof, m/z): 462.15 [M+H]+ tert-Butyl 4-(1-bromoimidazo[1,2-a]quinoxalin-4-yl)piperazine-1-carboxylate

Mw: 432.31 g/mol. 1H-NMR δ (ppm, 400 MHz, DMSO d6) 1.38 (s, 9H, 3×CH3 tBu), 3.45 (m, 4H, 2×CH2NBoc), 4.15 (m, 4H, 2×CH2NC=N), 7.28 (t, 1H, CH 7, J=8 Hz), 7.44 (t, 1H, CH 8, J=8 Hz), 7.54 (d, 1H, CH 9, J=8 Hz), 7.70 (d, 1H, CH 2, J=4 Hz), 8.93 (d, 1H, CH 6, J=8 Hz). 13C-NMR δ (ppm, 100 MHz, DMSO d6) 28.53 (CH3 tBu), 42.5 (CH2NBoc), 46.42 (CH2NC=N), 79.54 (Cq tBu), 99.64 (Cq 1), 114.97 (CH 6), 123.49 (CH 7), 126.11 (Cq 5'), 127.47 (CH 9, CH 8), 134.29 (CH 2), 134.66 (Cq 3'), 136.85 (Cq 9'), 147.33 (Cq 4), 154.43 (C=O carbamate). MS (ESI +, QTof, m/z): 432.10 [M+H]+ tert-Butyl (3-((1-bromoimidazo[1,2-a]quinoxalin-4-yl)amino)propyl)carbamate

Mw: 420.3 g/mol. 1H-NMR δ (ppm, 400 MHz, DMSO d6) 1.38 (s, 9H, 3×CH3 tBu), 1.74 (m, 2H, CH2CH2NHBoc), 3.00 (qd, 2H, CH2NHBoc, J=4 Hz), 3.56 (qd, 2H, CH2NH, J=4 Hz), 6.90 (m, 1H, NHBoc), 7.54 (m, 3H, CH 7, CH 8, CH 9), 7.73 (s, 1H, CH 2, J=4 Hz), 7.97 (m, 1H, NH), 9.04 (d, 1H, CH 6, J=8 Hz). 13C-NMR δ (ppm, 100 MHz, DMSO d6) 28.71 (CH3 tBu), 29.59 (CH2CH2NHBoc), 37.93 (CH2NH, CH2NHBoc), 77.95 (Cq tBu), 100.04 (Cq 1), 117.42 (CH 6), 126.66 (CH 7), 127.42 (Cq 5'), 128.59 (CH 8), 130.02 (CH 9), 134.03 (Cq 3'), 134.73 (CH 2), 137.24 (Cq 9'), 147.45 (Cq 4), 156.11 (C=O carbamate). MS (ESI +, QTof, m/z): 420.10 [M+H]⁺

1-Bromo-N-methyl-7-(trifluoromethyl)imidazo[1,2-a]quinoxalin-4-amine

Mw: 345.12 g/mol. 1H-NMR δ (ppm, 400 MHz, DMSO d6) 3.04 (d, 3H, CH3NH, J=8 Hz), 7.65 (m, 2H, CH 8), 7.78 (s, 1H, CH 2), 7.88 (s, 1H, CH 6), 8.11 (m, 1H, NHCH3), 9.12 (d, 1H, CH 9, J=8 Hz). 19F-NMR δ (ppm, 400 MHz, DMSO d6) −60.42.

1-Bromo-N-methyl-7-(trifluoromethoxy)imidazo[1,2-a]quinoxalin-4-amine

Mw: 361.12 g/mol. 1H-NMR δ (ppm, 400 MHz, DMSO d6) 3.02 (d, 3H, CH3NH, J=8 Hz), 7.30 (d, 1H, CH 8, J=8 Hz), 7.51 (s, 1H, CH 6), 7.73 (s, 1H, CH 2), 8.05 (m, 1H, NHCH3), 9.02 (d, 1H, CH 9, J=8 Hz). 13C-NMR δ (ppm, 100 MHz, DMSO d6) 27.70 (CH3NH), 99.85 (Cq 1), 114.79 (CH 8), 116.88 (CH 9), 119.34 (CH 6), 124.80 (Cq 5'), 134.19 (CH 2), 134.71 (Cq 3'), 139.55 (Cq 9'), 146.82 (Cq 7), 148.03 (Cq 4). 19F-NMR δ (ppm, 400 MHz, DMSO d6) −56.77. MS (ESI +, QTof, m/z): 360.99 [M+H]⁺

1-Bromo-N-methyl-8-(trifluoromethyl)imidazo[1,2-a]quinoxalin-4-amine

Mw: 345.12 g/mol. 1H-NMR δ (ppm, 400 MHz, DMSO d6) 3.04 (d, 3H, CH3NH, J=8 Hz), 7.75 (m, 3H, CH 2, CH 6, CH 7), 8.21 (m, 1H, NH), 9.24 (s, 1H, CH 9). 13C-NMR δ (ppm, 100 MHz, DMSO d6) 27.73 (CH3NH), 100.32 (Cq 1), 112.26 (CH 9), 123.63 (CH 7), 125.58 (Cq 5'), 127.81 (CH 6), 134.25 (Cq 3'), 134.83 (CH 2), 141.44 (Cq 9'), 149.02 (Cq 4). 19F-NMR δ (ppm, 100 MHz, DMSO d6) −59.89 (CF3).

tert-Butyl 2-((1-bromoimidazo[1,2-a]quinoxalin-4-yl)amino)acetate

Mw: 377.24 g/mol. 1H-NMR δ (ppm, 400 MHz, DMSO d6) 1.37 (s, 9H, 3×CH3 tBu), 4.11 (d, 2H, CH2 Gly, J=8 Hz), 7.34 (t, 1H, CH 7, J=8 Hz), 7.48 (t, 1H, CH 8, J=8 Hz), 7.61 (t, 1H, CH 9, J=8 Hz), 7.76 (s, 1H, CH 2), 8.02 (m, 1H, NH), 8.96 (d, 1H, CH 6, J=8 Hz). MS (ESI +, QTof, m/z): 377.0 [M+H]⁺

General Procedure for the Suzuki Cross-Coupling Reaction

The cross-coupling reaction of the brominated intermediate with the corresponding arylboronic acid (1.1 eq.) in the presence of tetrakis(triphenylphosphine)palladium catalyst is carried out under basic conditions (Na₂CO₃, 2 eq.), in a DME (10 mL)/H₂O (5 mL) mixture and under microwave assistance (140° C., 20 min). The reaction medium is filtered on Celite and washed with ethanol. The filtrate is concentrated and then purified by liquid chromatography on silica gel in order to obtain the desired compounds in pure form.

1-(3,4-Dimethoxyphenyl)-N-methylimidazo[1,2-a]quinoxalin-4-amine (EAPB 02203)

Coupling of 1-bromo-N-methylimidazo[1,2-a]quinoxalin-4-amine with 3,4-dimethoxyphenyl boronic acid (218 mg, 1.2 mmol). Yield 30%. 1H NMR (300 MHz, CDCl₃) δ: 7.78 (d, 1H), 7.38-7.29 (m, 3H), 7.10-6.91 (m, 4H), 6.28 (br s, 1H), 3.96 (s, 3H), 3.85 (s, 3H), 3.29 (s, 3H). 13C NMR (300 MHz, CDCl₃) δ: 152.61, 148.06, 142.74, 139.57, 131.53, 131.13, 129.56, 129.02, 127.60, 124.90, 124.47, 124.02, 122.1, 119.29, 116.74, 114.96, 110.49, 55.87, 29.20.

1-(3,5-Dimethoxyphenyl)-N-methylimidazo[1,2-a]quinoxalin-4-amine (EAPB 01803)

Coupling of 1-bromo-N-methylimidazo[1,2-a]quinoxalin-4-amine with 3,5-dimethoxyphenyl boronic acid (218 mg, 1.2 mmol). Yield 40%. 1H NMR (300 MHz, CDCl₃) δ: 7.79 (d, 1H), 7.42-7.39 (m, 2H), 7.32 (td, 1H), 6.97 (td, 1H), 6.64-6.60 (m, 3H), 6.29 (br s, 1H), 3.29 (s, 3H). 13C NMR (300 MHz, CDCl₃) δ: 163.62, 142.86, 139.57, 131.13, 130.54, 130.05, 129.02, 124.90, 124.47, 123.08, 114.96, 101.33, 98.38, 55.33, 29.26.

1-(3,4-Dimethoxyphenyl)imidazo[1,2-a]quinoxalin-4-amine (EAPB 02202)

Coupling of 1-bromoimidazo[1,2-a]quinoxalin-4-amine (262 mg, 0.997 mmol) with 3,4-dimethoxyphenyl boronic acid (199 mg, 1.096 mmol). Yield 15%. 1H NMR (300 MHz, CDCl₃) δ: 7.45-7.35 (m, 3H), 7.28 (d, 1H), 7.09 (d, 1H), 7.05-7.01 (m, 1H), 6.85-6.79 (m, 1H), 3.97 (s, 3H), 3.89 (s, 3H), 3.60 (s, 3H), 1.24 (s, 3H).

N-Methyl-1-(3,4,5-trimethoxyphenyl)imidazo[1,2-a]quinoxalin-4-amine (EAPB 02703)

Coupling of 1-bromo-N-methylimidazo[1,2-a]quinoxalin-4-amine with 3,4,5-trimethoxyphenyl boronic acid (365 mg, 2.17 mmol). Yield 28%. 1H NMR (300 MHz, CDCl₃) δ: 7.93-7.88 (m, 1H), 7.56-7.34 (m, 3H), 7.01 (t, 1H), 6.70 (s, 2H), 3.96 (s, 3H), 3.84 (s, 6H), 3.37 (br s, 3H). 13C NMR (300 MHz, CDCl₃) δ: 155.74, 142.86, 139.57, 136.68, 131.13, 129.38, 129.24, 129.02, 124.90, 124.75, 124.47, 123.08, 114.96, 103.91, 60.55, 56.22, 29.23.

tert-Butyl (2-((1-(3,4-dimethoxyphenyl)imidazo[1,2-a]quinoxalin-4-yl)amino)ethyl)carbamate (EAPB 02211)

Coupling of tertbutyl(2-((1-bromoimidazo[1,2-a]quinoxalin-4-yl)amino)ethyl)carbamate with 3,4-dimethoxyphenyl boronic acid. Yield: 57%. Mw: 463.53 g/mol. ¹H-NMR δ (ppm, 400 MHz, DMSO d6) 1.38 (s, 9H, 3×CH3 tBu), 3.27 (qd, 2H, CH2NHBoc, J=8 Hz), 3.63 (qd, 2H, CH2NH, J=8 Hz), 3.74 (s, 3H, OCH3), 3.87 (s, 3H, OCH3), 6.98 (m, 2H, NHBoc, CH 7), 7.16 (m, 3H, CH 2', CH 5', CH 6'), 7.30 (m, 2H, CH 8, CH 6), 7.49 (s, 1H, CH 2), 7.58 (d, 2H, CH 9, J=8 Hz), 7.71 (t, 1H, NH, J=4 Hz). 13C-NMR δ (ppm, 100 MHz, DMSO d6) 28.70 (CH3 tBu), 40.00 (CH2NHBoc, CH2NH), 56.05 (OCH3), 56.15 (OCH3), 78.10 (Cq tBu), 112.30 (CH 2'), 114.19 (CH 5'), 115.88 (CH 6'), 122.35 (Cq 1' phenyl), 122.76 (CH 7), 123.26 (CH 6'), 125.84 (Cq 5'), 126.49 (CH 8), 127.09 (CH 9), 130.85 (Cq 1), 132.42 (CH 2), 133.30 (Cq 3' quinoxaline), 138.06 (Cq 9'), 148.00 (Cq 3' phenyl), 149.25 (Cq 4' phenyl), 150.10 (Cq 4), 156.25 (C=O carbamate). MS (ESI +, QTof, m/z): 464.23 [M+H]⁺ tert-Butyl (6-((1-(3,4-dimethoxyphenyl)imidazo[1,2-a]quinoxalin-4-yl)amino)hexyl)carbamate (EAPB 02212)

Coupling of tertbutyl(6-((1-bromoimidazo[1,2-a]quinoxalin-4-yl)amino)hexyl)carbamate with 3,4-dimethoxyphenyl boronic acid. Yield: 61%. Mw: 519.64 g/mol. 1H-NMR δ (ppm, 400 MHz, DMSO d6) 1.31 to 1.40 (m, 15H, 3×CH3 tBu, CH2CH2CH2NH, CH2CH2CH2NHBoc, CH2CH2NHBoc), 1.66 (qt, 2H, CH2CH2NH, J=8 Hz), 2.91 (qd, 2H, CH2NHBoc, J=4 Hz), 3.53 (qd, 2H, CH2NH, J=4 Hz), 3.74 (s, 3H, OCH3), 3.87 (s, 3H, OCH3), 6.77 (t, 1H, NHBoc, J=4 Hz), 6.95 (t, 1H, CH 7, J=8 Hz), 7.10 (m, 3H, CH 2', CH 5', CH 6'), 7.28 (m, 2H, CH 6, CH8), 7.47 (s, 1H, CH 2), 7.57 (d, 1H, CH 9, J=8 Hz), 7.67 (t, 1H, NH, J=4 Hz). 13C-NMR δ (ppm, 100 MHz, DMSO d6) 26.5 and 26.72 (CH2CH2CH2NH, CH2CH2CH2NHBoc), 28.74 (CH3 tBu), 29.30 (CH2CH2NH), 29.97 (CH2CH2NHBoc), 40.00 (CH2NHBoc, CH2NH), 56.04 (OCH3), 56.14 (OCH3) 77.74 (Cq tBu), 112.28 (CH 2'), 114.23 (CH 5'), 115.85 (CH 6), 122.05 (CH 7), 122.84 (Cq 1'), 123.27 (CH 6'), 125.73 (Cq 5' quinoxaline), 126.44 (CH 8), 127.05 (CH 9), 130.79 (Cq 1), 132.31 (CH 2), 133.35 (Cq 3' quinoxaline), 138.31 (Cq 9'), 147.96 (Cq 3' phenyl), 149.24 (Cq 4' phenyl), 150.08 (Cq 4), 156.05 (C=O carbamate). MS (ESI +, QTof, m/z): 520.29 [M+H]$^+$ tert-Butyl 4-(1-(3,4-dimethoxyphenyl)imidazo[1,2-a]quinoxalin-4-yl)piperazine-1-carboxylate (EAPB 02213)

Coupling of tertbutyl 4-(1-bromoimidazo[1,2-a]quinoxalin-4-yl)piperazine-1-carboxylate with 3,4-dimethoxyphenyl boronic acid. Yield: 85%. Mw: 489.57 g/mol. 1H-NMR δ (ppm, 400 MHz, DMSO d6) 1.45 (s, 9H, 3×CH3 tBu), 3.53 (m, 4H, 2×CH2NBoc), 3.73 (s, 3H, OCH3), 3.87 (s, 3H, OCH3), 4.29 (m, 4H, 2×CH2NC=N), 7.05 (t, 1H, CH 7, J=8 Hz), 7.10 (d, 1H, CH 6'), 7.15 (m, 2H, CH 2', CH 5'), 7.30 (d, 1H, CH 6, J=8 Hz), 7.35 (t, 1H, CH 8, J=8 Hz), 7.56 (s, 1H, CH 2), 7.63 (d, 1H, CH 9, J=8 Hz). $^{13}$C-NMR δ (ppm, 100 MHz, DMSO d6) 28.56 (CH3 tBu), 43.00 (CH2NBoc), 46.40 (CH2NC=N), 56.07 (OCH3), 56.16 (OCH3), 79.54 (Cq tBu), 112.36 (CH 5'), 114.12 (CH 2'), 115.81 (CH 6), 122.79 (CH 7), 123.23 (CH 6', Cq 1'), 125.73 (Cq 5' quinoxaline), 126.44 (CH 8), 127.35 (CH 9), 130.36 (Cq 1), 132.51 (CH 2), 133.35 (Cq 3' quinoxaline), 136.91 (Cq 9'), 147.94 (Cq 3' phenyl), 149.33 (Cq 4' phenyl), 150.18 (Cq 4), 154.46 (C=O carbamate). MS (ESI +, QTof, m/z): 490.25 [M+H]$^+$ tert-Butyl (3-((1-(3,4-dimethoxyphenyl)imidazo[1,2-a]quinoxalin-4-yl)amino)propyl)carbamate (EAPB 02214)

Coupling of tertbutyl (3-((1-bromoimidazo[1,2-a]quinoxalin-4-yl)amino)propyl)carbamate with 3,4-dimethoxyphenyl boronic acid. Yield: 69%. Mw: 477.56 g/mol. 1H-NMR δ (ppm, 400 MHz, DMSO d6) 1.36 (s, 9H, 3×CH3 tBu), 1.77 (m, 1H, CH2CH2NHBoc), 3.02 (qd, 2H, CH2NHBoc, J=4 Hz), 3.56 (qd, 2H, CH2NH, J=4 Hz), 3.74 (s, 3H, OCH3), 3.89 (s, 3H, OCH3), 6.97 (m, 2H, CH 7, NHBoc), 7.17 (m, 3H, CH 6', CH 2', CH 5'), 7.29 (m, 2H, CH 6, CH 8), 7.49 (s, 1H, CH 2), 7.61 (m, 1H, CH 9). 13C-NMR δ (ppm, 100 MHz, DMSO d6) 28.73 (CH3 tBu), 29.80 (CH2CH2NHBoc), 37.91 (CH2NHBoc, CH2NH), 56.05 (OCH3), 56.15 (OCH3), 77.95 (Cq tBu), 112.30 (CH 5'), 114.22 (CH 2'), 115.92 (CH 6), 122.27 (Cq 1'), 123.28 (CH 7, CH 6'), 125.73 to 127.93 (CH 8, CH 9, Cq 5' quinoxaline), 130.85 (Cq 1), 132.43 (CH 2), 133.13 (Cq 3' quinoxaline), 139.56 (Cq 9'), 147.95 (Cq 3' phenyl), 149.25 (Cq 4' phenyl), 150.11 (Cq 4), 156.12 (C=O carbamate). MS (ESI +, QTof, m/z): 478.25 [M+H]$^+$ N-(1,3-Dihydroxy-2-(hydroxymethyl)propan-2-yl)-2-((1-(3,4-dimethoxyphenyl)imidazo[1,2-a]quinoxalin-4-yl)amino)acetamide (EAPB 02210)

Coupling of 2-(acetoxymethyl)-2-(2-((1-bromoimidazo[1,2-a]quinoxalin-4-yl)amino)acetamido)propane-1,3-diyl diacetate with 3,4-dimethoxyphenyl boronic acid. Yield: 16%. Mw: 481.50 g/mol. MS (ESI +, QTof, m/z): 482.20 [M+H]$^+$ 1-(3,4-Dimethoxyphenyl)-N-methyl-7-(trifluoromethyl)imidazo[1,2-a]quinoxalin-4-amine (EAPB 02203-7a)

Coupling of 1-bromo-N-methyl-7-(trifluoromethyl)imidazo[1,2-a]quinoxalin-4-amine with 3,4-dimethoxyphenyl boronic acid. Yield: 13%. Mw: 402.37 g/mol. 1H-NMR δ (ppm, 400 MHz, DMSO d6) 3.06 (d, 3H, CH3NH, J=8 Hz), 7.15 (m, 2H, CH 5', CH 6'), 7.20 (s, 1H, CH 2'), 7.33 (d, 1H, CH 8, J=8 Hz), 7.45 (d, 1H, CH 9, J=8 Hz), 7.54 (s, 1H, CH 2), 7.85 (s, 1H, CH 6), 8.05 (m, 1H, NCH3). 13C NMR δ (ppm, 100 MHz, DMSO d6) 27.72 (CH3NH), 56.03 (OCH3), 56.16 (OCH3), 112.37 (CH 5'), 114.01 (CH 2'), 117.09 (CH 9), 118.97 (CH 8), 122.18 (Cq 1'), 122.88 (CH 6, CH 6'), 125.85 (Cq 5'), 131.29 (Cq 1), 132.82 (CH 2), 133.01 (Cq 3'), 137.53 (Cq 9'), 138.47 (Cq 7), 149.27 (Cq 3', Cq 4'), 150.22 (Cq 4). 19F-NMR δ (ppm, 400 MHz, DMSO d6). MS (ESI +, QTof, m/z): 403.00 [M+H]$^+$ 1-(3,4-Dimethoxyphenyl)-N-methyl-7-(trifluoromethoxy)imidazo[1,2-a]quinoxalin-4-amine (EAPB 02203-7b)

Coupling of 1-bromo-N-methyl-7-(trifluoromethoxy)imidazo[1,2-a]quinoxalin-4-amine with 3,4-dimethoxyphenyl boronic acid. Yield: 67%. Mw: 418.37 g/mol. 1H-NMR δ (ppm, 400 MHz, DMSO d6) 3.08 (d, 3H, CH3NH, J=8 Hz), 3.77 (s, 3H, OCH3), 3.88 (s, 3H, OCH3), 7.01 (d, 1H, CH 8, J=8 Hz), 7.12 (d, 1H, CH 6', J=8 Hz), 7.17 (d, 1H, CH 5', J=8 Hz), 7.20 (s, 1H, CH 2'), 7.36 (d, 1H, CH 9), 7.48 (s, 1H, CH 6), 7.51 (d, 1H, CH 2, J=4 Hz), 8.02 (d, 1H, NHCH3, J=4 Hz). 13C-NMR δ (ppm, 100 MHz, DMSO d6) 27.75 (CH3NH), 56.01 (OCH3), 56.14 (OCH3), 112.34 (CH 5'), 114.14 (CH 2'), 114.59 (CH 8), 117.23 (CH 9), 117.97 (CH 6), 122.35 (Cq 1'), 123.29 (CH 6'), 124.01 (Cq 5'), 131.01 (Cq 1), 132.56 (CH 2), 133.24 (Cq 3'), 139.82 (Cq 9'), 146.29 (Cq 7), 149.27 and 149.36 (Cq 4' phenyl, Cq 3' phenyl), 150.20 (Cq 4). 19F-NMR δ (ppm, 100 MHz, DMSO d6) −56.86 (OCF3). MS (ESI+, QTof, m/z): 419.20 [M+H]$^+$ 1-(3,4-Dimethoxyphenyl)-N-methyl-7-(carbonitrile) imidazo[1,2-a]quinoxalin-4-amine (EAPB 02203-7c)

Coupling of 1-bromo-N-methyl-7-(carbonitrile)imidazo[1,2-a]quinoxalin-4-amine with 3,4-dimethoxyphenyl boronic acid. Yield <10%. Mw: 359.38 g/mol. 1H-NMR δ (ppm, 400 MHz, DMSO d6) 3.08 (d, 3H, CH3NH, J=8 Hz), 3.77 (s, 3H, OCH3), 3.88 (s, 3H, OCH3), 7.01 (d, 1H, CH 8, J=8 Hz), 7.12 (d, 1H, CH 6', J=8 Hz), 7.17 (d, 1H, CH 5', J=8 Hz), 7.20 (s, 1H, CH 2'), 7.36 (d, 1H, CH 9), 7.48 (s, 1H, CH 6), 7.51 (d, 1H, CH 2, J=4 Hz), 8.02 (d, 1H, NHCH3, J=4 Hz). MS (ESI +, QTof, m/z): 360.15 [M+H]+

1-(3,4-Dimethoxyphenyl)-N-methyl-8-(trifluoromethyl)imidazo[1,2-a]quinoxalin-4-amine (EAPB 02203-8a)

Coupling of 1-bromo-N-methyl-8-(trifluoromethyl)imidazo[1,2-a]quinoxalin-4-amine with 3,4-dimethoxyphenyl boronic acid. Yield: 21%. Mw: 402.37 g/mol. 1H-NMR δ (ppm, 400 MHz, DMSO d6) 2.94 (d, 3H, CH3NH), 3.75 (s, 3H, OCH3), 3.86 (s, 3H, OCH3), 7.16 (m, 2H, CH 5', CH 6'), 7.23 (s, 1H, CH 2'), 7.55 (s, 1H, CH 2), 7.59 (m, 2H, CH 7, CH 9), 7.72 (d, 1H, CH 6, J=8 Hz), 8.16 (m, 1H, NH). 13C-NMR δ (ppm, 100 MHz, DMSO d6) 29.42 (CH3NH), 56.18 (OCH3), 56.24 (OCH3), 112.55 (CH 5'), 113.31 (CH 9), 114.22 (CH 2'), 122.12 (Cq 1'), 122.85 (CH 7), 123.46 (CH 6'), 125.11 (Cq 5'), 127.53 (CH 6), 131.21 (Cq 1), 132.53 (CH 2), 133.36 (Cq 3' imidazole), 141.46 (Cq 9'), 142.5 (Cq 8), 149.55 (Cq 3' phenyl, Cq 4' phenyl), 150.47 (Cq 4). $^{19}$F-NMR δ (ppm, 100 MHz, DMSO d6) −60.28. MS (ESI +, QTof, m/z): 403.00 [M+H]+ tert-Butyl 2-((1-(3,4-dimethoxyphenyl)imidazo[1,2-a]quinoxalin-4-yl)amino)acetate (EAPB 02216)

Coupling of tertbutyl 2-((1-bromoimidazo[1,2-a]quinoxalin-4-yl)amino) with 3,4-dimethoxyphenyl boronic acid. Yield: 19%. Mw: 434.49 g/mol. 1H-NMR δ (ppm, 400 MHz, DMSO d6) 1.44 (s, 9H, 3×CH3 tbu), 3.74 (s, 3H, OCH3), 3.87 (s, 3H, OCH3), 4.13 (d, 2H, CH2 Gly, J=8 Hz), 7.01 (t, 1H, CH 7), 7.14 (m, 3H, CH 2', CH 5', CH 6'), 7.31 (m, 2H, CH 6, CH 8), 7.52 (s, 1H, CH 2), 7.54 (m, 1H, CH 9), 7.98 (m, 1H, NH). MS (ESI +, QTof, m/z): 435.20 [M+H]+

General Procedure for the Deprotection Reaction

The protected compound is solubilized in dichloromethane. Under inert atmosphere at 0° C. and vigorous stirring, boron tribromide is added (2 eq. per function to be deprotected). Once the addition is finished, the reaction medium is stirred for 1 h 30 m at room temperature. It is then hydrolyzed with saturated sodium bicarbonate solution at 0° C. The aqueous phase is extracted three times with dichloromethane, dried over sodium sulfate, filtered and concentrated. The crude reaction product is purified by chromatography on silica column to provide the expected products.

1-(3,4-Dihydroxyphenyl)imidazo[1,2-a]quinoxalin-4-amine (EAPB 02302)

Yield 25%. 1H NMR (300 MHz, DMSO-d$_6$) δ: 9.41 (s, 1H), 9.31 (s, 1H), 7.53 (dd, 1H), 7.44 (s, 1H), 7.37-7.28 (m, 2H), 7.21 (m, 2H), 7.04-6.98 (m, 1H), 6.92-6.89 (m, 2H), 6.82 (dd, 1H). 13C NMR (300 MHz, DMSO-d$_6$) δ: 149.02, 146.58, 145.54, 137.52, 132.45, 131.85, 130.87, 125.93, 125.86, 125.61, 121.80, 121.55, 120.78, 117.39, 115.98, 115.40.

1-(3,4-Dihydroxyphenyl)-N-methylimidazo[1,2-a]quinoxalin-4-amine (EAPB 02303)

Yield 17%. 1H NMR (300 MHz, DMSO-d$_6$) δ: 7.65 (q, 1H), 7.58 (dd, 1H), 7.38-7.29 (m, 3H), 6.97 (m, 1H), 6.90-6.86 (m, 2H), 6.80 (dd, 1H), 3.04 (d, 3H). 13C NMR (300 MHz, DMSO-d$_6$) δ: 148.03, 146.51, 145.48, 137.76, 132.76, 131.45, 130.59, 126.47, 125.84, 125.26, 121.55, 121.49, 120.78, 117.36, 115.92, 115.33, 27.22.

1-(3,5-Dihydroxyphenyl)-N-methylimidazo[1,2-a]quinoxalin-4-amine (EAPB 01903)

Yield 33%. $^1$H NMR (300 MHz, MeOD) δ: 7.71 (dd, 1H), 7.52 (dd, 1H), 7.41 (s, 1H), 7.36 (td, 1H), 7.04 (td, 1H), 6.46-6.40 (m, 3H), 3.22 (s, 3H).

4-(4-((2-Aminoethyl)amino)imidazo[1,2-a]quinoxalin-1-yl)benzene-1,2-diol (EAPB 02306)

Yield: 94%. Mw: 335.36 g/mol. 1H-NMR δ (ppm, 400 MHz, DMSO d6) 3.14 (m, 2H, CH2NH2), 3.81 (m, 2H, CH2NH), 6.79 (d, 1H, CH 6', J=8 Hz), 6.90 (s, 1H, CH 2'), 6.94 (d, 1H, CH 5', J=8 Hz), 7.01 (t, 1H, CH 7, J=8 Hz), 7.31 (m, 2H, CH 8, CH 6), 7.43 (s, 1H, CH 2), 7.60 (d, 1H, CH 9, J=8 Hz), 7.87 (t, 1H, NH, J=4 Hz). 13C-NMR δ (ppm, 100 MHz, DMSO d6) 40.00 (CH2NH2, CH2NH), 115.83 (CH 6), 116.52 (CH 5'), 117.86 (CH 2'), 121.05 (Cq 1'), 121.96 (CH 6'), 122.71 (CH 7), 125.95 (Cq 5'), 126.52 (CH 8), 127.13 (CH 9), 131.34 (Cq 1), 132.13 (CH 2), 133.02 (Cq 3' quinoxaline), 137.65 (Cq 9'), 146.04 (Cq 3' phenyl), 147.10 (Cq 4' phenyl), 148.13 (Cq 4). MS (ESI +, QTof, m/z): 336.15 [M+H]+

2-((1-(3,4-Dihydroxyphenyl)imidazo[1,2-a]quinoxalin-4-yl)amino)ethylammonium chloride (EAPB 02306s)

Mw: 371.82 g/mol. 1H-NMR δ (ppm, 400 MHz, DMSO d6) 3.18 (m, 2H, CH2NH3), 4.05 (m, 2H, CH2NH), 6.80 (d, 1H, CH 6', J=8 Hz), 6.94 (s, 1H, CH 2'), 6.99 (d, 1H, CH 5', J=8 Hz), 7.14 (t, 1H, CH 7, J=8 Hz), 7.33 (m, 1H, CH 6), 7.39 (m, 1H, CH 8), 7.52 (s, 1H, CH 2), 7.60 (d, 1H, CH 9, J=8 Hz), 8.05 (m, 1H, CH 9), 8.27 (m, 3H, NH3). 13C-NMR δ (ppm, 100 MHz, DMSO d6) 40.00 (CH2NH3, CH2NH), 116.22 (CH 6), 116.69 (CH 5'), 117.73 (CH 2'), 120.06 (Cq 1'), 122.03 (CH 6'), 124.34 (CH 7), 125.75 (Cq 5'), 127.19 (CH 8, CH 9), 132.23 (CH 2), 132.93 to 133.22 (Cq 1, Cq 3' quinoxaline, Cq 9'), 146.18 (Cq 3' phenyl), 146.68 (Cq 4' phenyl), 147.46 (Cq 4). MS (ESI +, QTof, m/z): 336.15 [M+H]+

4-(4-((6-Aminohexyl)amino)imidazo[1,2-a]quinoxalin-1-yl)benzene-1,2-diol (EAPB 02307)

Yield: 81%. Mw: 391.47 g/mol. 1H-NMR δ (ppm, 400 MHz, DMSO d6) 1.39 (m, 4H, CH2CH2CH2NH, CH2CH2CH2NH2), 1.54 (m, 2H, CH2CH2CH2NH2), 1.69 (m, 2H, CH2CH2NH), 2.76 (m, 2H, CH2NH2), 3.57 (m, 2H, CH2NH), 6.79 (d, 1H, CH 6', J=8 Hz), 6.88 (s, 1H, CH 2'), 6.93 (d, 1H, CH 5', J=8 Hz), 6.97 (t, 1H, CH 7), 7.29 (m, 2H, CH 6, CH8), 7.39 (s, 1H, CH 2), 7.54 (d, 1H, CH 9, J=8 Hz), 7.64 (t, 1H, NH, J=4 Hz). 13C-NMR δ (ppm, 100 MHz, DMSO d6) 26.08 and 26.53 (CH2CH2CH2NH, CH2CH2CH2NH2), 27.47 (CH2CH2NH2), 29.16 (CH2CH2NH), 40.00 (CH2NH2, CH2NH), 115.85 (CH 6), 116.46 (CH 5'), 117.89 (CH 2'), 121.26 (Cq 1'), 122.09 (CH 7, CH 6'), 125.75 (Cq 5'), 126.41 (CH 8), 126.99 (CH 9), 131.22 (Cq 1), 131.96 (CH 2), 133.14 (Cq 3'), 138.24 (Cq 9'), 146.02 (Cq 3' phenyl), 147.05 (Cq 4' phenyl), 147.97 (Cq 4). MS (ESI +, QTof, m/z): 392.21 [M+H]+

6-((1-(3,4-Dihydroxyphenyl)imidazo[1,2-a]quinoxalin-4-yl)amino)hexan-1-ammonium chloride (EAPB 02307s)

Mw: 427.93 g/mol. 1H-NMR δ (ppm, 400 MHz, DMSO d6) 1.39 (m, 4H, CH2CH2CH2NH, CH2CH2CH2NH2), 1.59 (m, 2H, CH2CH2NH2), 1.73 (m, 2H, CH2CH2NH), 2.77 (m, 2H, CH2NH2), 3.85 (m, 2H, CH2NH), 6.81 (d, 1H, CH 6', J=8 Hz), 6.95 (s, 1H, CH 2'), 6.99 (d, 1H, CH 5', J=8 Hz), 7.22 (t, 1H, CH 7, J=8 Hz), 7.34 (d, 1H, CH 6, J=8 Hz), 7.45 (t, 1H, CH 8, J=8 Hz), 7.68 (s, 1H, CH 2), 7.97 (m, 3H, NH3), 8.35 (m, 1H, CH 9). 13C-NMR δ (ppm, 100 MHz, DMSO d6) 25.95 and 26.03 (CH2CH2CH2NH, CH2CH2CH2NH2), 27.23 (CH2CH2NH2), 28.44 (CH2CH2NH), 40.00 (CH2NH2, CH2NH), 116.57 (CH 6), 116.71 (CH 5'), 117.61 (CH 2'), 119.60 (CH 9), 120.16 (Cq 1'), 121.82 (CH 6'), 124.19 (CH 7), 125.21 (Cq 5'), 127.52 (CH 8), 131.73 (Cq 1), 134.10 to 134.20 (CH 2, Cq 3' quinoxaline, Cq 9'), 144.88 (Cq 3' phenyl), 146.27 (Cq 4' phenyl), 147.69 (Cq 4). MS (ESI +, QTof, m/z): 392.21 [M+H]$^+$

4-(4-(Piperazin-1-yl)imidazo[1,2-a]quinoxalin-1-yl)benzene-1,2-diol (EAPB 02308)

Yield: 54%. Mw: 361.40 g/mol. 1H-NMR δ (ppm, 400 MHz, DMSO d6) 3.09 (m, 4H, 2×CH2NH), 4.40 (m, 2H, 2×CH2NC=N), 6.79 (d, 1H, CH 6', J=8 Hz), 6.88 (s, 1H, CH 2'), 6.92 (d, 1H, CH 5', J=8 Hz), 7.06 (t, 1H, CH 7, J=8 Hz), 7.35 (m, 3H, CH 6, CH 8, NH), 7.49 (s, 1H, CH 2), 7.60 (d, 1H, CH 9, J=8 Hz). MS (ESI +, QTof, m/z): 362.16 [M+H]$^+$

4-(4-((3-Aminopropyl)amino)imidazo[1,2-a]quinoxalin-1-yl)benzene-1,2-diol (EAPB 02309)

Yield: 80%. Mw: 349.39 g/mol. 1H-NMR δ (ppm, 400 MHz, DMSO d6) 2.02 (m, 2H, CH2), 2.90 (m, 2H, CH2), 3.64 (m, 2H, CH2), 6.80 (d, 1H, CH 6', J=8 Hz), 6.91 (m, 2H, CH 2', CH 5'), 6.99 (t, 1H, CH 7, J=8 Hz), 7.30 (m, 3H, CH 6, CH 8, NH), 7.43 (s, 1H, CH 2), 7.60 (d, 1H, CH 9, J=8 Hz), 7.90 (m, 2H, NH2), 9.31 (m, 1H, NH). MS (ESI +, QTof, m/z): 350.16 [M+H]$^+$

4-(4-(Methylamino)-7-(trifluoromethyl)imidazo[1,2-a]quinoxalin-1-yl)benzene-1,2-diol (EAPB 02303-7a)

Yield: 28%. Mw: 374.32 g/mol. 1H-NMR δ (ppm, 400 MHz, DMSO d6) 3.06 (d, 3, CH3NH, J=8 Hz), 6.81 (d, 1H, CH 6', J=8 Hz), 6.89 (s, 1H, CH 2'), 6.92 (d, 1H, CH 5', J=8 Hz), 7.34 (d, 1H, CH 8, J=8 Hz), 7.47 (s, 1H, CH 2), 7.51 (d, 1H, CH 9, J=8 Hz), 7.82 (s, 1H, CH 6), 8.03 (m, 1H, NHCH3). MS (ESI +, QTof, m/z): 375.10 [M+H]$^+$

4-(4-(Methylamino)-7-(trifluoromethoxy)imidazo[1,2-a]quinoxalin-1-yl)benzene-1,2-diol (EAPB 02303-7b)

Yield: 67%. Mw: 390.32 g/mol. 1H-NMR δ (ppm, 400 MHz, DMSO d6) 3.08 (d, 3H, CH3NH, J=8 Hz), 6.84 (d, 1H, CH 6', J=8 Hz), 6.94 (s, 1H, CH 2'), 6.97 (d, 1H, CH 5', J=8 Hz), 7.03 (d, 1H, CH 8, J=8 Hz), 7.40 (d, 1H, CH 9, J=8 Hz), 7.42 (s, 1H, CH 2), 7.45 (s, 1H, CH 6), 8.01 (d, 1H, NHCH3, J=4 Hz). 13C-NMR δ (ppm, 100 MHz, DMSO d6) 27.74 (CH3NH), 114.58 (CH8), 116.56 (CH 5'), 117.15 (CH 9), 117.72 (CH 2'), 118.12 (CH 6), 120.80 (Cq 1'), 121.99 (CH 6'), 124.76 (Cq 5'), 131.38 (Cq 1), 132.20 (CH 2), 133.04 (Cq 3'), 139.79 (Cq 9'), 146.12 (Cq 3' phenyl), 146.25 (Cq 7), 147.18 (Cq 4' phenyl), 149.27 (Cq 4). 19F-NMR δ (ppm, 100 MHz, DMSO d6) −56.83 (OCF3). MS (ESI +, QTof, m/z): 391.10 [M+H]$^+$

4-(4-(Methylamino)-8-(trifluoromethyl)imidazo[1,2-a]quinoxalin-1-yl)benzene-1,2-diol (EAPB 02303-8a)

Yield: 55%. Mw: 374.32 g/mol. 1H-NMR δ (ppm, 400 MHz, DMSO d6) 3.12 (d, 3H, CH3NH, J=8 Hz), 6.83 (d, 1H, CH 6', J=8 Hz), 6.91 (s, 1H, CH 2'), 6.96 (d, 1H, CH 5'), 7.55 (s, 1H, CH 2), 7.60 (s, 1H, CH 9), 7.67 (d, 1H, CH 7, J=8 Hz), 7.82 (d, 1H, CH 6). 13C-NMR δ (ppm, 100 MHz, DMSO d6) 28.38 (CH3NH), 113.45 (CH 9), 116.52 (CH 5'), 118.50 (CH 2'), 120.08 (Cq 1'), 121.93 (CH 1'), 123.11 (CH 7), 125.08 (Cq 5'), 132.68 to 132.75 (CH 2, Cq 1, Cq 3', Cq 9'), 146.36 (Cq 3' phenyl, Cq 4' phenyl), 147.49 (Cq 4). 19F-NMR δ (ppm, 100 MHz, DMSO d6) −60.44 (CF3). MS (ESI +, QTof, m/z): 375.20 [M+H]$^+$

(2S)-2-((1-(3,4-Dimethoxyphenyl)imidazo[1,2-a]quinoxalin-4-yl)amino)propanoic acid (EAPB 02219)

Yield: 11%. Mw: 392.41 g/mol. MS (ESI +, QTof, m/z): 393.0 [M+H]$^+$

(2S)-2-((1-(3,4-Dimethoxyphenyl)imidazo[1,2-a]quinoxalin-4-yl)amino)-3-methylbutanoic acid (EAPB 02221)

Yield: 13%. Mw: 420.46 g/mol. MS (ESI +, QTof, m/z): 421.1 [M+H]$^+$

(2S)-2-Amino-5-((1-(3,4-dihydroxyphenyl)imidazo[1,2-a]quinoxalin-4-yl)amino)pentanoic acid (EAPB 02325)

Yield: 20%. Mw: 407.42 g/mol. MS (ESI +, QTof, m/z): 408.1 [M+H]$^+$

Biology: Study of the Activity of the Compounds on 15 Tumor Lines, In Vitro Cytotoxicity Study The goal of this protocol is to study the effects of the compounds on the proliferation of various human cancer cell lines in order to evaluate the $EC_{50}$ and their activity in cellulo.

Protocol

The cells are seeded the day before treatment in 96 well plates. Each compound concentration is tested in triplicate. A 96 well plate can contain 3 compounds.

Cell suspensions for each cancer cell line are prepared in culture medium with a specific density of the specific cell (see the following table). Then, 1004 of cell suspension is spread per well (plate per one cell line).

TABLE 1

Cancer cell lines tested

| Cell line | Organism | Tissue origin | Cell type | Cell nb/well | Culture medium |
|---|---|---|---|---|---|
| A375 | *Homo sapiens*, human | Skin | Malignant melanoma | 5,000 | 10% DMEM |
| CFPAC-1 | *Homo sapiens*, human | Colon; from the sub-clavicular metastatic region | Adenocarcinoma | 13,000 | 10% RPMI |
| PC-3 | *Homo sapiens*, human | Prostate (from the metastatic site: bone) | Adenocarcinoma, grade IV | 10,000 | 10% RPMI |
| AsPC-1 | *Homo sapiens*, human | Pancreas; ascites | Adenocarcinoma | 13,000 | 10% RPMI |
| BxPC3 | *Homo sapiens*, human | Pancreas | Carcinoma | 5,000 | 10% RPMI |
| A2058 | *Homo sapiens*, human | Melanoma | Malignant melanoma | 7,500 | 10% DMEM |
| Calu-1 | *Homo sapiens*, human | Lung; from the metastatic site: pleura | Carcinoma | 7,500 | 10% DMEM |
| LoVo | *Homo sapiens*, human | Colon, metastatic region: sub-clavicular region | Adenocarcinoma | 5,000 | 10% DMEM |
| MEWO | *Homo sapiens*, human | Skin | Malignant melanoma | 7,500 | 10% DMEM |
| T-47D | *Homo sapiens*, human | Breast; mammary gland (from pleural effusion) | Ductal carcinoma | 10,000 | 10% DMEM |
| Capan-1 | *Homo sapiens*, human | Pancreas (from the metastatic site: liver) | Adenocarcinoma | 10,000 | 10% RPMI |
| HepG2 | *Homo sapiens*, human | Liver | Hepatoblastoma (hepatocellular carcinoma) | 13,000 | 10% RPMI |
| IPC298 | *Homo sapiens*, human | Melanoma | Malignant melanoma | 5,000 | 10% RPMI |
| PF382 | *Homo sapiens*, human | Hematopoietic and lymphoid tissue | Lymphoid neoplasm | 100,000 | 10% RPMI (SUSPENSION) |
| COLO-205 | *Homo sapiens*, human | Colon; ascites: from the metastatic site | Dukes D colorectal adenocarcinoma | 7,500 | 10% RPMI (½ SUSPENSION) |

Preparation of the Compounds

Stock solutions of the tested compounds are prepared at 10 mM in 100% DMSO and stored at 20° C.

The in vitro activity studies of the compounds were evaluated on various types of tumors and showed activity of the same order of magnitude between EAPB02303 and EAP02302 and systematically superior in relation to the activity of EAPB0503 [i.e., (1-(3-methoxyphenyl)-N-methylimidazo[1,2-a]quinoxalin-4-amine)].

TABLE 2

Study of inhibition of cell growth in vitro on 15 tumor lines by EAPB0503, EAPB02303 and EAPB02302.

| | | EC$_{50}$ (nM) | | |
|---|---|---|---|---|
| Tissue origin | Cell line | EAPB0503 | EAPB02303 | EAPB02302 |
| Melanoma | IPC298 | 469 | 40 | 75 |
| | A375 | 383 | 10 | 60 |
| | A2058 | 185 | 4 | 13 |
| | MEWO | 125 | 3 | 10 |
| Pancreas | CFPAC-1 | 598 | 12 | 67 |
| | AsPC-1 | 2799 | 957 | 1818 |
| | Capan-1 | 561 | 154 | 206 |
| | BxPC3 | 159 | 11 | 25 |
| Colon | LoVo | 89 | 45 | 44 |
| | COLO-205 | 201 | 38 | 44 |
| Lung | Calu-1 | 196 | 4 | 14 |
| Prostate | PC-3 | 537 | 12 | 56 |
| Breast | T-47D | 198 | 13 | 78 |
| Lymphoid | PF382 | 205 | 7 | 29 |
| Liver | HepG2 | 1358 | 247 | 267 |

TABLE 3

Summarized results 1:

| | EC$_{50}$ (nM) | | |
|---|---|---|---|
| Cell line | EAPB0503 | EAPB02303 | EAPB02302 |
| A375 | 383 | 10 | 60 |
| CFPAC-1 | 598 | 12 | 67 |
| PC-3 | 537 | 12 | 56 |
| BxPC3 | 159 | 11 | 25 |
| A2058 | 185 | 4 | 13 |
| Calu-1 | 196 | 4 | 14 |
| LoVo | 89 | 45 | 44 |
| MEWO | 125 | 3 | 10 |
| T-47D | 198 | 13 | 78 |
| AsPC-1 | 2799 | 957 | 1818 |
| PF382 | 205 | 7 | 29 |
| Capan-1 | 561 | 154 | 206 |
| COLO-205 | 201 | 38 | 44 |
| IPC298 | 469 | 40 | 75 |
| HepG2 | 1358 | 247 | 267 |

TABLE 4

Summarized results 2

| Compounds | Structure | IC$_{50}$ (nM) |
|---|---|---|
| CPA 8 | [structure: 1-bromo-imidazo[1,2-a]quinoxaline with NHCH$_3$] | 2354 |
| EAPB 02303 | [structure: 3,4-dihydroxyphenyl-imidazo[1,2-a]quinoxaline with NHCH$_3$] | <3 |
| EAPB 02211 | [structure: 3,4-dimethoxyphenyl-imidazo[1,2-a]quinoxaline with NH-CH$_2$CH$_2$-NHBoc] | >10000 |
| EAPB 02212 | [structure: 3,4-dimethoxyphenyl-imidazo[1,2-a]quinoxaline with NH-(CH$_2$)$_2$-NHBoc, isomer] | >10000 |
| EAPB 02306 | [structure: 3,4-dihydroxyphenyl-imidazo[1,2-a]quinoxaline with NH-CH$_2$CH$_2$-NH$_2$] | 1284 |

TABLE 4-continued
Summarized results 2
| Compounds | Structure | $IC_{50}$ (nM) |
|---|---|---|
| EAPB 02307 | 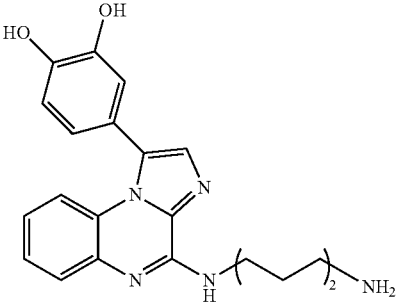 | 5694 |
| EAPB 02306s | 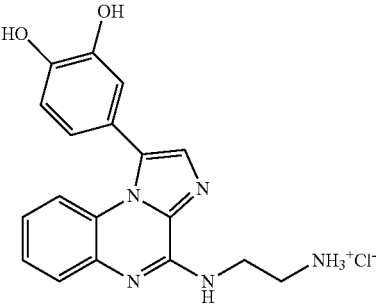 | 1704 |
| EAPB 02213 | 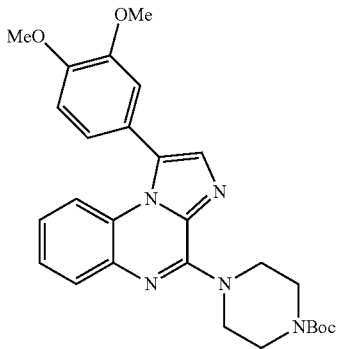 [SMILES: COc1ccc(-c2cnc3c(N4CCN(C(=O)OC(C)(C)C)CC4)nc4ccccc4n23)cc1OC] | >10000 |
| EAPB 02214 | 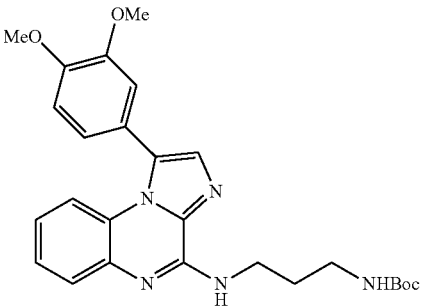 [SMILES: COc1ccc(-c2cnc3c(NCCCNC(=O)OC(C)(C)C)nc4ccccc4n23)cc1OC] | >10000 |

TABLE 4-continued
Summarized results 2
| Compounds | Structure | IC$_{50}$ (nM) |
|---|---|---|
| EAPB 02203-7b | 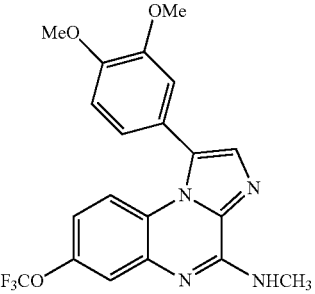 [SMILES: CNc1nc2cc(OC(F)(F)F)ccc2n2c(-c3ccc(OC)c(OC)c3)cnc12] | 3493 |
| EAPB 02303-7b | 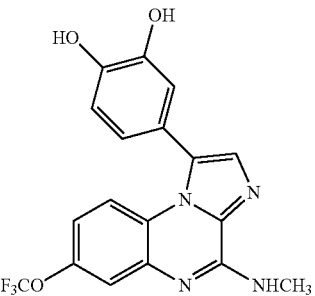 [SMILES: CNc1nc2cc(OC(F)(F)F)ccc2n2c(-c3ccc(O)c(O)c3)cnc12] | 199 |
| EAPB 02303-7c | 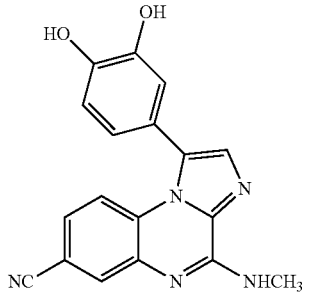 [SMILES: CNc1nc2cc(C#N)ccc2n2c(-c3ccc(O)c(O)c3)cnc12] | 6388 |
| EAPB 02310 | 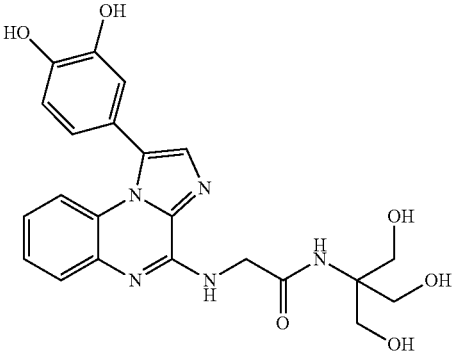 [SMILES: O=C(CNc1nc2ccccc2n2c(-c3ccc(O)c(O)c3)cnc12)NC(CO)(CO)CO] | >10000 |

TABLE 4-continued

Summarized results 2

| Compounds | Structure | IC$_{50}$ (nM) |
|---|---|---|
| EAPB0 2308 | 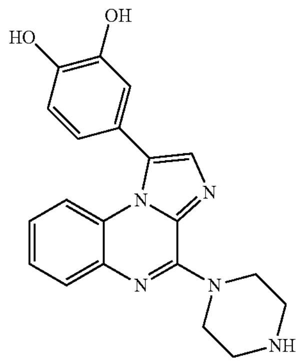 [SMILES: Oc1ccc(-c2cnc3c(N4CCNCC4)nc4ccccc4n23)cc1O] | >10000 |
| EAPB 02303-7a | 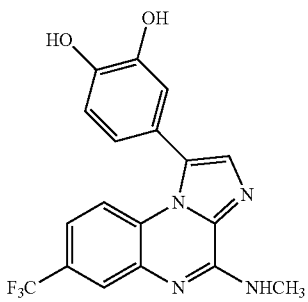 [SMILES: CNc1nc2cc(C(F)(F)F)ccc2n2c(-c3ccc(O)c(O)c3)cnc12] | 6909 |
| EAPB 02309 | 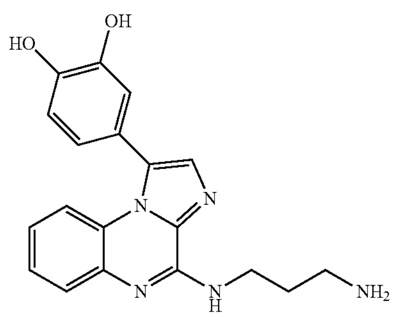 [SMILES: NCCCNc1nc2ccccc2n2c(-c3ccc(O)c(O)c3)cnc12] | 5588 |
| EAPB 02203-8a | 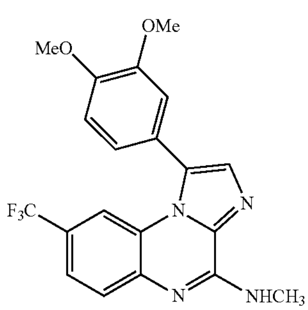 [SMILES: CNc1nc2ccc(C(F)(F)F)cc2n2c(-c3ccc(OC)c(OC)c3)cnc12] | >10000 |

TABLE 4-continued

Summarized results 2

| Compounds | Structure | IC$_{50}$ (nM) |
|---|---|---|
| EAPB 02303-8b | (structure) | >10000 |
| EAPB 02303-8a | (structure) | >10000 |
| EAPB 02220 | (structure) | >10000 |
| EAPB 02218 | (structure) | >10000 |

TABLE 4-continued

Summarized results 2

| Compounds | Structure | IC$_{50}$ (nM) |
|---|---|---|
| EAPB 02222 | (structure: 1-(3,4-dimethoxyphenyl)-imidazo[1,2-a]quinoxaline with NH-CH(CH$_2$CH(CH$_3$)$_2$)-C(O)-OtBu substituent) | >10000 |
| PED 26 | (structure: imidazo[1,2-a]quinoxaline with NHCH$_3$) | >10000 |
| EAPB 02203 | (structure: 1-(3,4-dimethoxyphenyl)-imidazo[1,2-a]quinoxaline with NHCH$_3$) | 193 |

The EC$_{50}$ values (concentration causing 50% inhibition of the specific activity of the control) are determined by nonlinear regression analysis of the inhibition curve produced by the average of the replicated values (use of a sigmoidal dose-response curve with the Hill slope as variable and the constant values of 0.0 for the base and 100.0 for the peak as constraints). The analysis is carried out by using the GraphPad PRISM 5.0 software.

Materials and Methods

Day 1: the cells are seeded one day before treatment with the compounds in 96 well plates. Cell suspensions for each cancer cell line are prepared with a specific density in a specific culture medium (see preceding table). Next, 100₄ of cell suspension is distributed per well (1×96 well plate per cell line).

Day 2: 24 hours later, the negative compounds or controls (DMSO) are added to the cells (100₄ of a compound solution in its specific medium with a final DMSO concentration of 0.15%).

Each compound concentration is tested in triplicate (6 concentrations between 10$^{-9}$ M and 10$^{-5}$ M per compound). The cells are incubated at 37° C. for 72 hours with no new treatment.

Day 5: 15 minutes before incubation of the cells with MTT (3-[4,5-dimethylthiazol-2-yl]-2,5-diphenyltetrazolium bromide), 10% SDS is added to the control wells to obtain a final concentration of 1%. The positive control of inhibition of proliferation is 1% SDS.

Once the medium is removed, 100₄ of a solution of MTT in fresh medium is added to each well (10 µL of 10×MTT solution at 5 mg/mL in PBS +90₄ of fresh medium) and the plates are incubated for 4 hours at 37° C.

The MTT reaction is quenched and the medium is homogenized by addition of 100₄ of 10% SDS/0.01 M HCl solution placed in each well. The medium is incubated for 2 hours at 37° C. before measuring its absorbance. Absorbance is measured at 570 nm.

Study of the Effect of the Compounds on the Polymerization of Purified Tubulin.

Tubulin is prepared from pig brain according to the purification process described by Williams and Lee (1982). Tubulin polymerization is monitored by turbidimetry at 350 nm with an MC2 spectrophotometer (Safas, Monaco) equipped with a heat-jacketed cuvette holder. The reaction mixture was prepared at 0° C., and contains PEM buffer, 25% glycerol (v/v), 1 mM GTP, and 2.4 µM tubulin. The GTP and the tubulin are added at the last minute. Stock solutions of the tested compounds and of colchicine are prepared in DMSO at the desired concentration, and 14 of the compound solution is added to the reaction medium. The same volume of DMSO alone was used as a negative control. The final volume of the sample is 200₄. The reaction is initiated by placing the cuvette in the cell compartment of the spectrophotometer thermostated at 37° C. Ice is added 45 minutes later to launch depolymerization in order to confirm the specificity of the signal.

The invention claimed is:
1. A compound of the general formula (I):

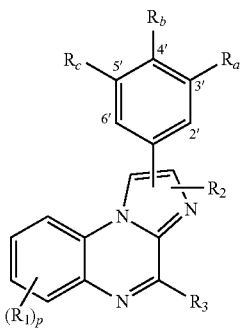

(I)

wherein:
R$_1$ represents a hydrogen atom;
R$_2$ represents a hydrogen atom;
R$_3$ is selected from the group consisting of amino, C$_1$-C$_3$ alkylamino, and C$_1$-C$_3$ dialkylamino;
R$_a$ and R$_b$ are hydroxy groups and R$_c$ represents a hydrogen atom;
p being 1, 2, 3 or 4;
or a pharmaceutically acceptable salt thereof.

2. The compound as claimed in claim 1, characterized in that it has the formula (II):

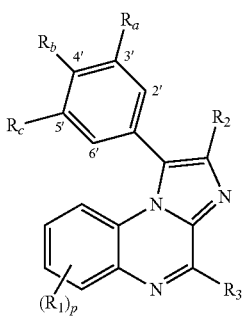

(II)

wherein the various R$_1$, R$_2$, R$_3$, R$_a$, R$_b$, R$_c$ and p groups are as defined in claim 1,
or a pharmaceutically acceptable salt thereof.

3. The compound as claimed in claim 1 characterized in that it has the formula (III):

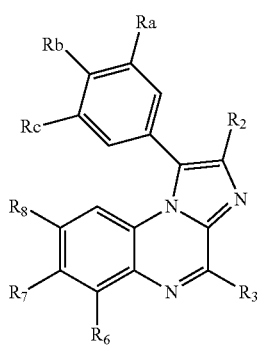

(III)

wherein the various R$_2$, R$_3$, R$_a$, R$_b$ and R$_c$ groups are as defined in claim 1,
R$_6$, R$_7$ and R$_8$ independently represent a hydrogen atom;
or a pharmaceutically acceptable salt thereof.

4. The compound as claimed in claim 1 characterized in that it has the formula (IV):

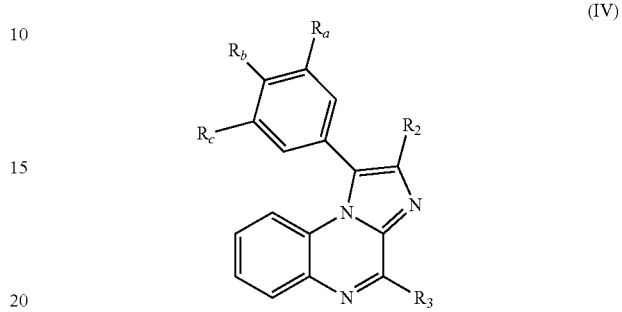

(IV)

wherein the various R$_2$, R$_3$, R$_a$, R$_b$ and R$_c$ groups are as defined in claim 1;
or a pharmaceutically acceptable salt thereof.

5. The compound as claimed in claim 1, characterized in that the compound is:
1. 1-(3,4-Dihydroxyphenyl)imidazo[1,2-a]quinoxalin-4-amine, or
2. 1-(3,4-Dihydroxyphenyl)-N-methylimidazo[1,2-a]quinoxalin-4-amine.

6. The compound as claimed in claim 1 characterized in that:
R$_3$ is a methylamino or amine group.

7. A method for manufacturing the compound as claimed in claim 1, characterized in that said method comprises:
a step of coupling a compound of formula (V):

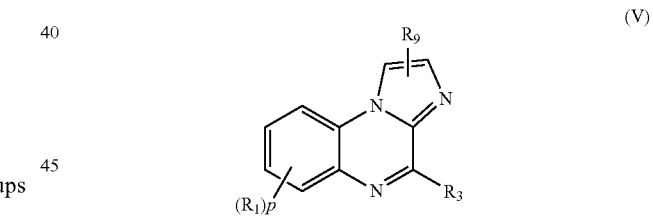

(V)

wherein R$_1$, R$_3$ and p are as defined in claim 1; and
R$_9$ is a halogen atom;
with a suitable arylboronic acid, under Suzuki conditions; and
recovering, extracting and/or purifying the compound of claim 1.

8. A pharmaceutical composition comprising at least one compound as claimed in claim 1 and optionally a pharmaceutically acceptable carrier.

9. The compound as claimed in claim 1 as a medicinal product.

10. A method for the treatment of at least one cancer comprising administering an effective amount of a compound of claim 1 to a subject in need thereof.

11. The method of claim 10 characterized in that the cancer is solid or liquid, optionally metastatic or secondary.

12. The method of claim 10 characterized in that the cancer is a melanoma, a cancer of the pancreas, colon or prostate, a lymphoma, a leukemia or a myeloma.

13. The method of claim 10 characterized in that the cancer is cancer of the breast, prostate, lungs, esophagus, skin, bladder, stomach, liver, uterus, colon or rectum.

14. The method of claim 10 characterized in that the cancer is cancer of the blood or of certain blood cells such as lymphocytes or leukocytes.

* * * * *